US012611444B2

(12) United States Patent
Guo et al.

(10) Patent No.: US 12,611,444 B2
(45) Date of Patent: Apr. 28, 2026

(54) IL-36 CYTOKINE EXPRESSING ONCOLYTIC VIRUSES FOR TREATING CANCER

(71) Applicant: UNIVERSITY OF PITTSBURGH—OF THE COMMONWEALTH SYSTEM OF HIGHER EDUCATION, Pittsburgh, PA (US)

(72) Inventors: Zong Sheng Guo, Wexford, PA (US); Binfeng Lu, Pittsburgh, PA (US); David L. Bartlett, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 1078 days.

(21) Appl. No.: 17/696,978

(22) Filed: Mar. 17, 2022

(65) Prior Publication Data

US 2022/0211814 A1 Jul. 7, 2022

Related U.S. Application Data

(63) Continuation of application No. PCT/US2020/051467, filed on Sep. 18, 2020.

(60) Provisional application No. 62/903,346, filed on Sep. 20, 2019.

(51) Int. Cl.

| | |
|---|---|
| *A61K 35/768* | (2015.01) |
| *A61K 35/15* | (2015.01) |
| *A61K 35/17* | (2015.01) |
| *A61K 35/742* | (2015.01) |
| *A61K 38/20* | (2006.01) |
| *A61K 39/00* | (2006.01) |
| *A61K 39/395* | (2006.01) |
| *A61P 35/00* | (2006.01) |
| *C12N 15/863* | (2006.01) |

(52) U.S. Cl.
CPC .............. *A61K 38/20* (2013.01); *A61K 35/15* (2013.01); *A61K 35/17* (2013.01); *A61K 35/742* (2013.01); *A61K 35/768* (2013.01); *A61K 39/0011* (2013.01); *A61K 39/3955* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 2007/0077231 A1 | 4/2007 | Contag et al. | |
| 2015/0250837 A1* | 9/2015 | Nolin ................... | A61K 35/761 |
| | | | 435/235.1 |
| 2017/0020938 A1 | 1/2017 | Wang et al. | |
| 2018/0318229 A1* | 11/2018 | Frederick ............... | A61K 39/39 |

FOREIGN PATENT DOCUMENTS

| | | |
|---|---|---|
| CN | 108 524 918 A | 9/2018 |
| WO | WO 2016/009017 A1 | 1/2016 |
| WO | WO 2018/191619 A1 | 10/2018 |
| WO | WO 2019/093435 A1 | 5/2019 |
| WO | WO 2019/099483 A1 | 5/2019 |

OTHER PUBLICATIONS

Downs-Canner et al., Phase 1 Study of Intravenous Oncolytic Poxvirus (vvDD) in Patients With Advanced Solid Cancers, Molecular Therapy, 2016, pp. 1492-1501.*
Geng et al., Viral and non-viral vectors in gene therapy: current state and clinical perspectives, eBioMedicine, 2025, pp. 1-12.*
Wang et al., IL-36γ transforms the tumor microenvironment and promotes type 1 lymphocyte-mediated antitumor immune responses , Cancer Cell. Sep. 1, 20154; 28(3): 296-306.*
Baker et al., "IL-1 Family Members in Cancer; Two Sides to Every Story," Frontiers In Immunology, 10:1197 (2019) 16 pgs.
Chen et al., "Targeted codelivery of doxorubicin and IL-36γ expression plasmid for an optimal chemo-gene combination therapy against cancer lung metastasis," Nanomedicine: Nanotechnology, Biology, and Medicine, Elsevier, Amsterdam, NL, 15:129-141 (2019).
Yang et al., "IL-36γ-armed oncolytic virus exerts superior efficacy through induction of potent adaptive antitumor immunity," Cancer Immunology Immunotherapy, Springer, Berlin/Heidelberg, 70:2467-2481 (2021).
Andtbacka et al., "Talimogene Laherparepvec Improves Durable Response Rate in Patients With Advanced Melanoma," J Clin Oncol 33:2780-2788 (2015).
Bartlett et al., "Oncolytic viruses as therapeutic cancer vaccines," Mol Cancer 12:103 (2013).
Bassoy et al., "Regulation and function of interleukin-36 cytokines," Immunol Rev 281:169-178 (2018).
Bidgood et al., "Cloak and Dagger: Alternative Immune Evasion and Modulation Strategies of Poxviruses," Viruses 7:4800-4825 (2015).
Bowie et al., "A46R and A52R from vaccinia virus are antagonists of host IL-1 and toll-like receptor signaling," Proc Natl Acad Sci USA 97:10162-10167 (2000).
Bronte et al., "Effective Genetic Vaccination with a Widely Shared Endogenous Retroviral Tumor Antigen Requires CD40 Stimulation during Tumor Rejection Phase," J Immunol 171:6396-6405 (2003).

(Continued)

*Primary Examiner* — Maria Marvich
(74) *Attorney, Agent, or Firm* — Baker Botts L.L.P.

(57) ABSTRACT

The present disclosure provides interleukin-36 (IL-36) cytokine (e.g., IL-36γ) expressing oncolytic viruses, and compositions comprising thereof. The present disclosure further provides methods of using said oncolytic viruses and compositions for treating cancer, and for improving a subject's responsiveness to an immunomodulatory agent.

11 Claims, 26 Drawing Sheets

Specification includes a Sequence Listing.

(56) References Cited

OTHER PUBLICATIONS

Chakrabarti et al., "Compact, Synthetic, Vaccinia Virus Early/Late Promoter for Protein Expression," Biotechniques 23:1094-1097 (1997).

Cochran et al., "In Vitro Mutagenesis of the Promoter Region for a Vaccinia Virus Gene: Evidence for Tandem Early and Late Regulatory Signals," J. Virol. 54:30-37 (1985).

Downs-Canner et al., "Phase 1 Study of Intravenous Oncolytic Poxvirus (vvDD) in Patients with Advanced Solid Cancers," Mol Ther 24(8):1492-1501 (2016).

Myers et al., "Optimal alignments in linear space," Comput. Appl. Biosci., 4:11-17 (1988).

Farber et al., "Human memory T cells: generation, compartmentalization and homeostasis," Nat Rev Immunol 14:24-35 (2014).

Foulds et al., "Expression of a suppressive p15E-related epitope in colorectal and gastric cancer," Br J Cancer 68:610-616 (1993).

Gajewski et al., "Innate and adaptive immune cells in the tumor microenvironment," Nat Immunol 14:1014-1022 (2013).

Gresnigt et al., "The IL-36 receptor pathway regulates *Aspergillus fumigatus*-induced Th1 and Th17 responses," Eur J Immunol 43:416-426 (2013).

Guo et al., "The combination of immunosuppression and carrier cells significantly enhances the efficacy of oncolytic poxvirus in the pre-immunized host," Gene Ther 17:1465-1475 (2010).

Guo et al., "Vaccinia virus-mediated cancer immunotherapy: cancer vaccines and oncolytics," J Immunother Cancer 7:6 (2019) 21 pgs.

Guo et al., "Rapid Generation of Multiple Loci-Engineered Marker-free Poxvirus and Characterization of a Clinical-Grade Oncolytic Vaccinia Virus," Mol Ther Methods Clin Dev 7:112-122 (2017).

Heo et al., "Randomized dose-finding clinical trial of oncolytic immunotherapeutic vaccinia JX-594 in liver cancer," Nat Med 19:329-336 (2013).

Huang et al., "The immunodominant major histocompatibility complex class I-restricted antigen of a murine colon tumor derives from an endogenous retroviral gene product," Proc Natl Acad Sci USA 93:9730-9735 (1996).

Kaufman et al., "Oncolytic viruses: a new class of immunotherapy drugs," Nat Rev Drug Discov 14:642-662 (2015).

Kershaw et al., "Immunization against Endogenous Retroviral Tumor-associated Antigens," Cancer Res 61(21):7920-7924 (2001).

Lawler et al., "Oncolytic Viruses in Cancer Treatment A Review," JAMA Oncol 3:841-849 (2017).

Li et al., "The Efficacy of Oncolytic Adenovirus Is Mediated by T-cell Responses against Virus and Tumor in Syrian Hamster Model," Clin Cancer Res 23:239-249 (2016).

Lian et al., "The Double-Stranded RNA Analogue Polyinosinic-Polycytidylic Acid Induces Keratinocyte Pyroptosis and Release of IL-36γ," J Invest Dermatol 132:1346-1353 (2012).

Lichty et al., "Going viral with cancer immunotherapy," Nat Rev Cancer 14:559-567 (2014).

Liu et al., "Rational combination of oncolytic vaccinia virus and PD-L1 blockade works synergistically to enhance therapeutic efficacy," Nat Commun 8:14754 (2017).

Liu et al., "Modifying the cancer-immune set point using vaccinia virus expressing re-designed interleukin-2," Nat Commun 9:4682 (2018).

Lu et al., "Interleukin-33 in tumorigenesis, tumor immune evasion, and cancer immunotherapy," J Mol Med 94:535-543 (2016).

McCart et al., "Systemic Cancer Therapy with a Tumor-selective Vaccinia Virus Mutant Lacking Thymidine Kinase and Vaccinia Growth Factor Genes," Cancer Res 61:8751-8757 (2001).

McCart et al., "Complex interactions between the replicating oncolytic effect and the enzyme/prodrug effect of vaccinia mediated tumor regression," Gene Ther 7:1217-1223 (2000).

Moutaftsi et al., "A consensus epitope prediction approach identifies the breadth of murine TCD8+-cell responses to vaccinia virus," Nat Biotechnol 24:817-819 (2006).

Mutamba et al., "Expression of IL-1Rrp2 by human myelomonocytic cells is unique to DCs and facilitates DC maturation by IL-1F8 and IL-1F9," Eur J Immunol 42:607-617 (2012).

Nagarsheth et al., "Chemokines in the cancer microenvironment and their relevance in cancer immunotherapy," Nat Rev Immunol 17:559-572 (2017).

Needleman et al., "A General Method Applicable to the Search for Similarities in the Amino Acid Sequence of Two Proteins," J. Mol. Biol. 48:444-453 (1970).

Ribas et al., "Cancer Immunotherapy Using Checkpoint Blockade," Science 359:1350-1355 (2018).

Ricca et al., "Pre-existing Immunity to Oncolytic Virus Potentiates Its Immunotherapeutic Efficacy," Mol Ther 26:1008-1019 (2018).

Vigne et al., "IL-36R ligands are potent regulators of dendritic and T cells," Blood 118:5813-5823 (2011).

Sallusto et al., "Central Memory and Effector Memory T Cell Subsets: Function, Generation, and Maintenance," Annu Rev Immunol 22:745-763 (2004).

Samson et al., "Intravenous Delivery of Oncolytic Reovirus to Brain Tumor Patients Immunologically Primes for Subsequent Checkpoint Blockade," Sci Transl Med 10(422):25 pgs. (2018).

Shitaoka et al., "Identification of Tumoricidal TCRs from Tumor-Infiltrating Lymphocytes by Single-Cell Analysis," Cancer Immunol Res 6:378-388 (2018).

Smith et al., "Vaccinia virus immune evasion: mechanisms, virulence and immunogenicity," J Gen Virol 94:2367-2392 (2013).

Staib et al., "Inactivation of the viral interleukin 1β receptor improves CD8+ T-cell memory responses elicited upon immunization with modified vaccinia virus Ankara," J Gen Virol 86:1997-2006 (2005).

Wang et al., "IL-36γ Transforms the Tumor Microenvironment and Promotes Type 1 Lymphocyte-Mediated Antitumor Immune Responses," Cancer Cell 28:296-306 (2015).

Weinstein et al., "Tbet and IL-36γ cooperate in therapeutic DC-mediated promotion of ectopic lymphoid organogenesis in the tumor microenvironment," OncoImmunology 6(6):e1322238 (2017).

Wolfl et al., "Activation-induced expression of CD137 permits detection, isolation, and expansion of the full repertoire of CD8+ T cells responding to antigen without requiring knowledge of epitope specificities," Blood 110:201-210 (2007).

Yang et al., "A new recombinant vaccinia with targeted deletion of three viral genes: its safety and efficacy as an oncolytic virus," Gene Ther 14:638-647 (2007).

Ye et al., "CD137 accurately identifies and enriches for naturally-occurring tumor-reactive T cells in tumor," Clin Cancer Res 20:44-55 (2014).

Zafar et al., "Intravenously usable fully serotype 3 oncolytic adenovirus coding for CD40L as an enabler of dendritic cell therapy," OncoImmunology 6:e1265717 (2017).

Zamarin et al., "Intratumoral modulation of the inducible co-stimulator ICOS by recombinant oncolytic virus promotes systemic anti-tumour immunity," Nat Commun 8:14340 (2017).

Zamarin et al., "Localized Oncolytic Virotherapy Overcomes Systemic Tumor Resistance to Immune Checkpoint Blockade Immunotherapy," Sci Transl Med 6:226ra32 (2014).

Zeh et al., "High Avidity CTLs for Two Self-Antigens Demonstrate Superior In Vitro and In Vivo Antitumor Efficacy," J Immunol 162:989-994 (1999).

Zeh et al., "First-in-man Study of Western Reserve Strain Oncolytic Vaccinia Virus: Safety, Systemic Spread, and Antitumor Activity," Mol Ther 23:202-214 (2015).

* cited by examiner

| Mice with MC38–luc tumor | Challenged with MC38–luc (right flank) | Challenged with Lewis lung cancer (left flank) |
|---|---|---|
| Cured by vvTK– (n=6) | 0/6 | 4/6 |
| Cured with vvTK–IL36γ (n=9) | 0/9 | 2/9 |
| Naïve mice (n=5) | 5/5 | 5/5 |

Panc02–luc i.p. tumor

Survival (%)

PBS vvTD vvTD–IL36γ

Time (days)

B16 s.q. tumor

Survival (%)

PBS vvTK– vvTK–IL36γ vvTD vvTD–IL36γ

Time (days)

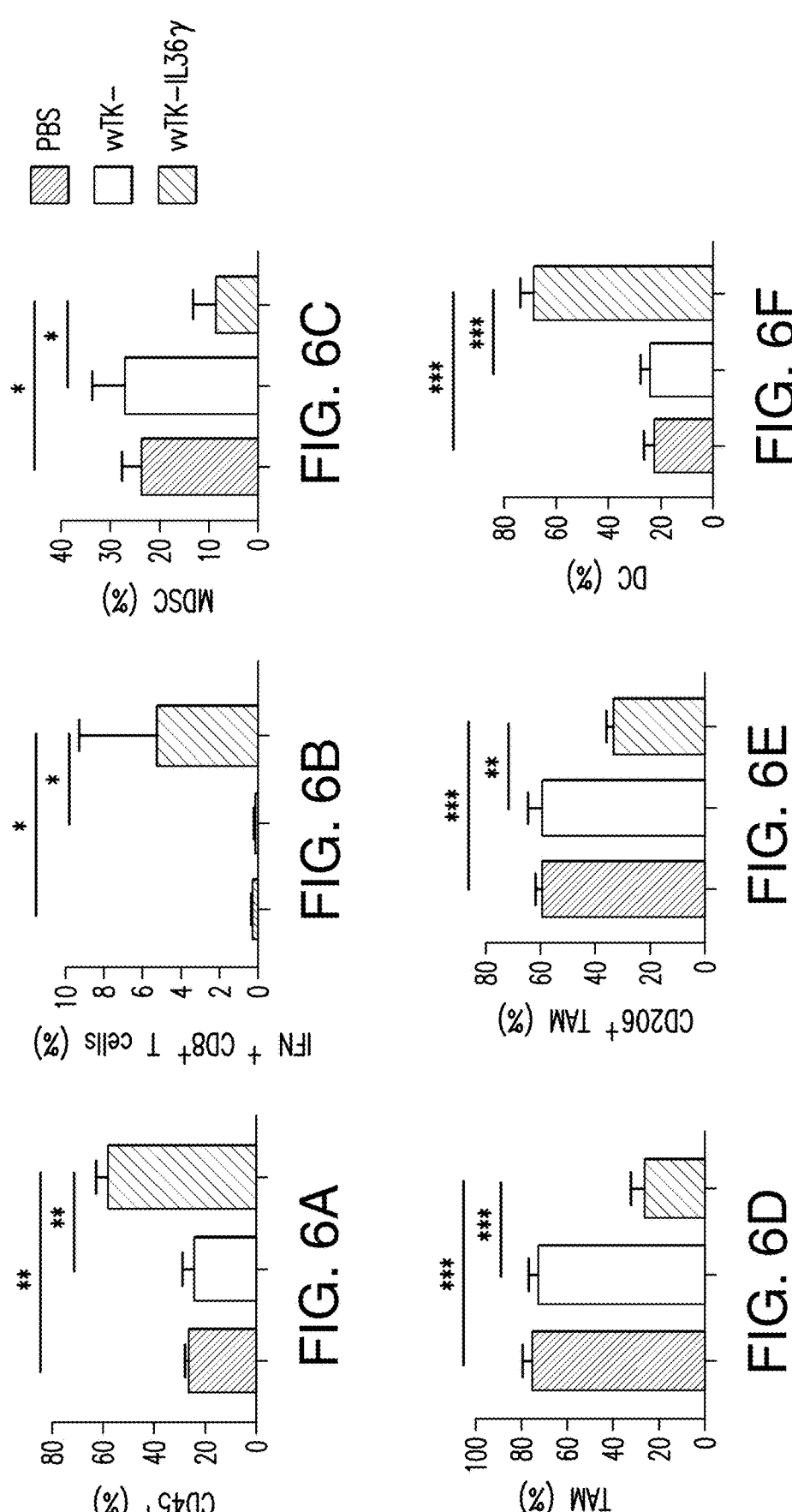

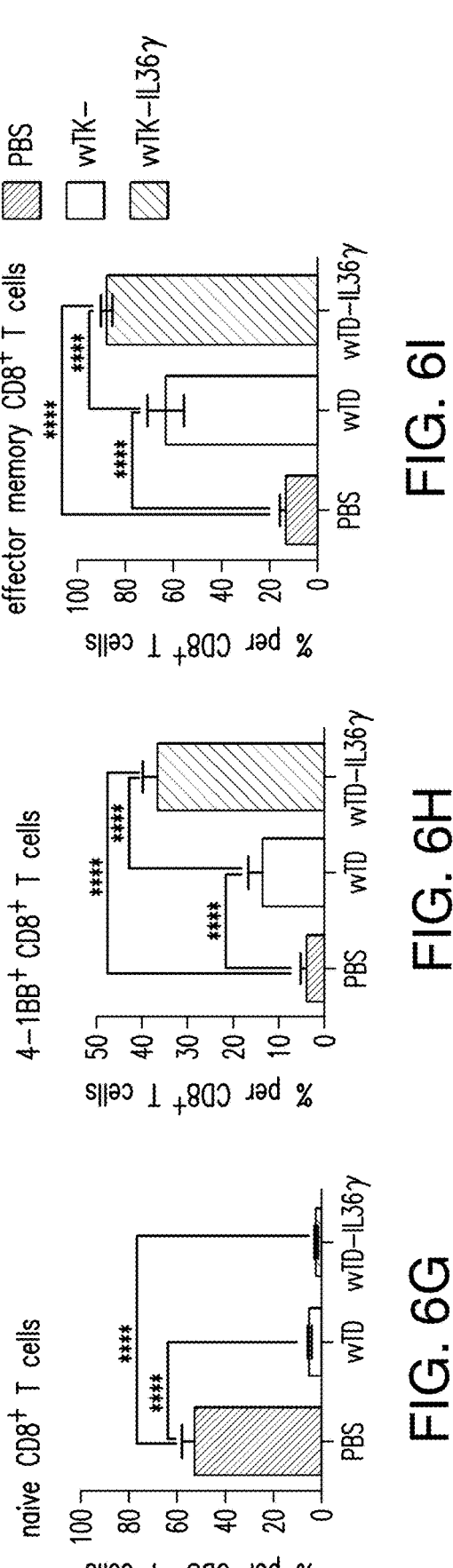

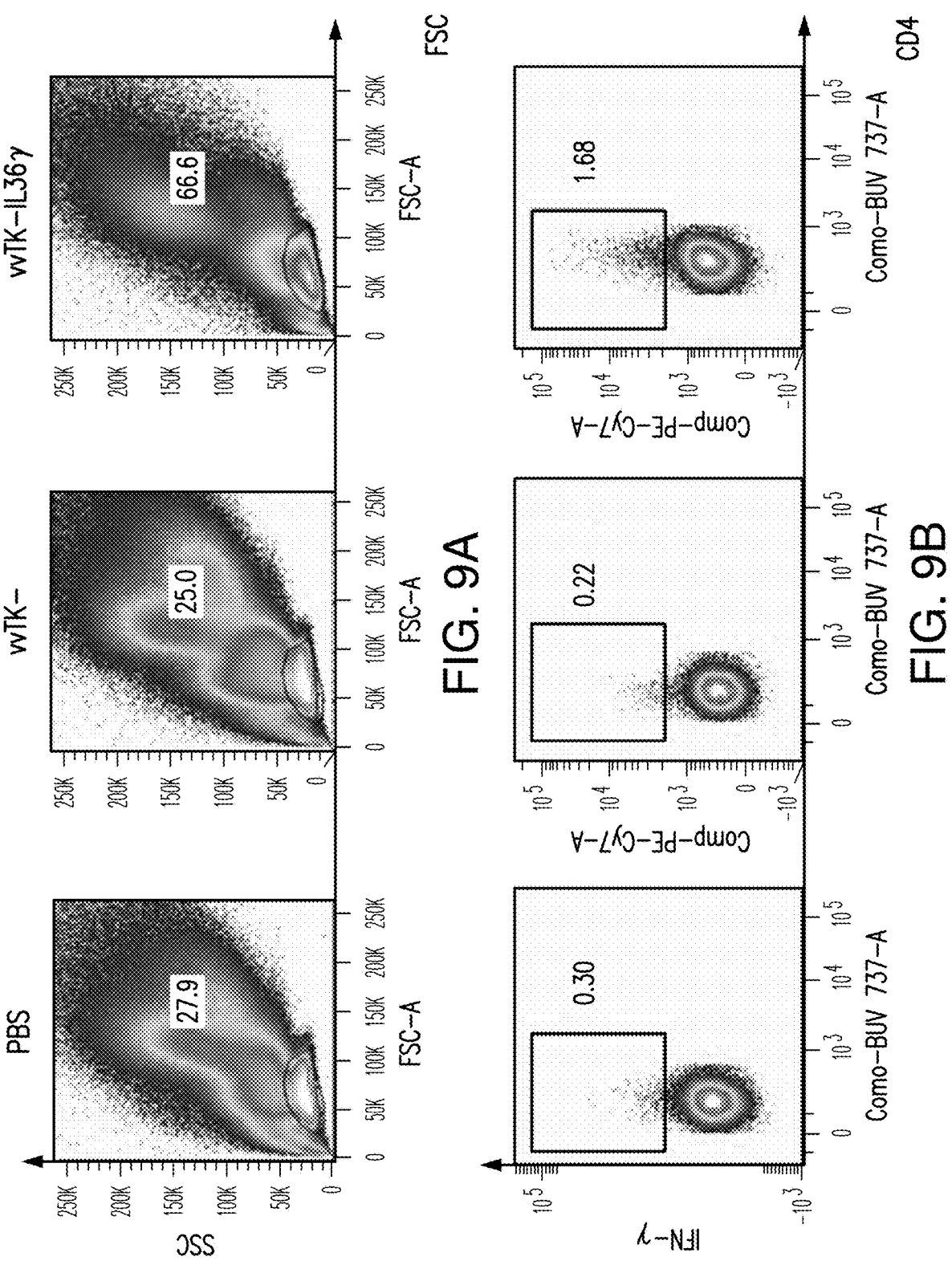

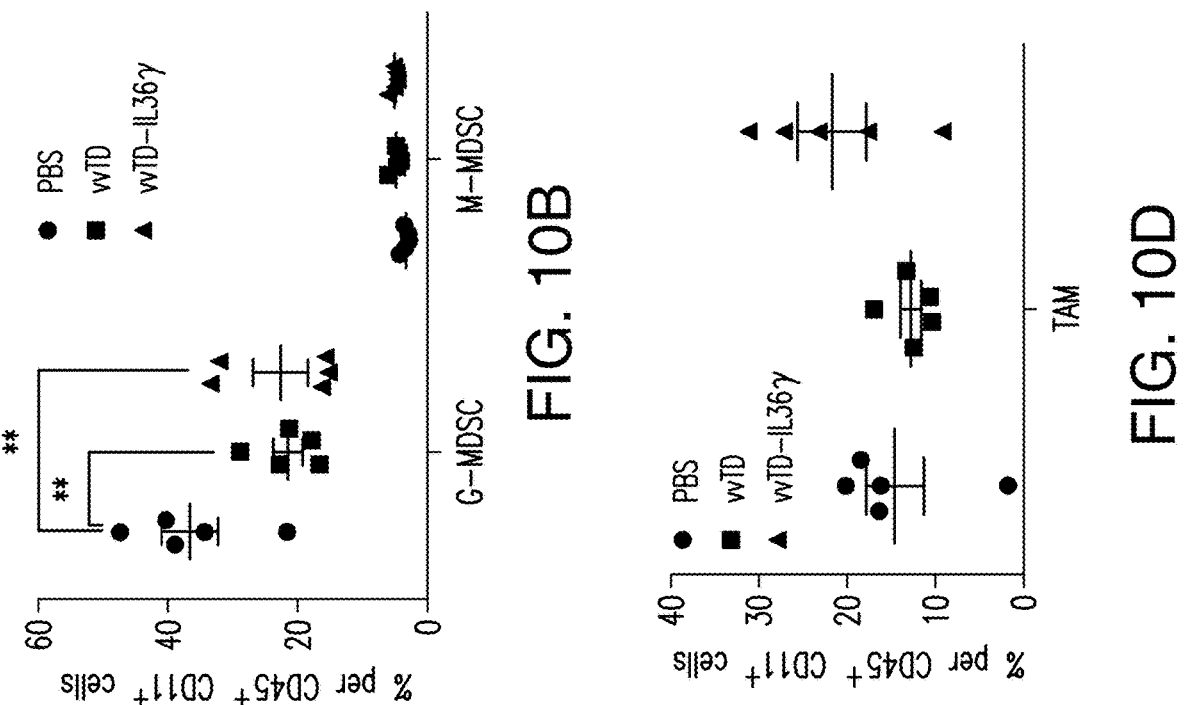
FIG. 10B
FIG. 10A
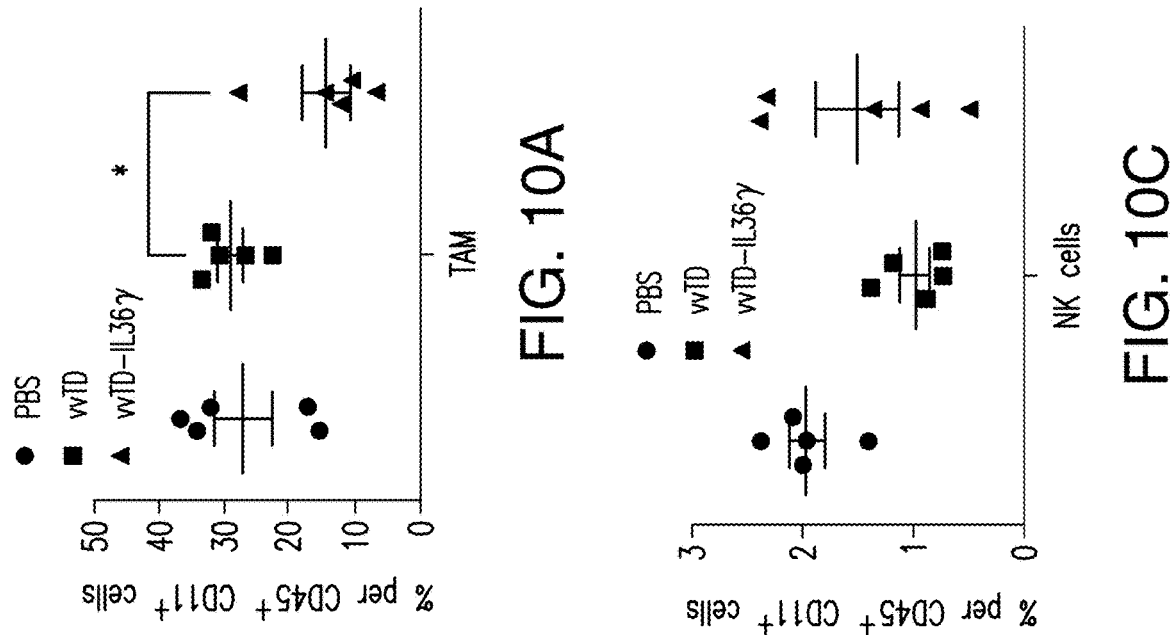
FIG. 10D
FIG. 10C

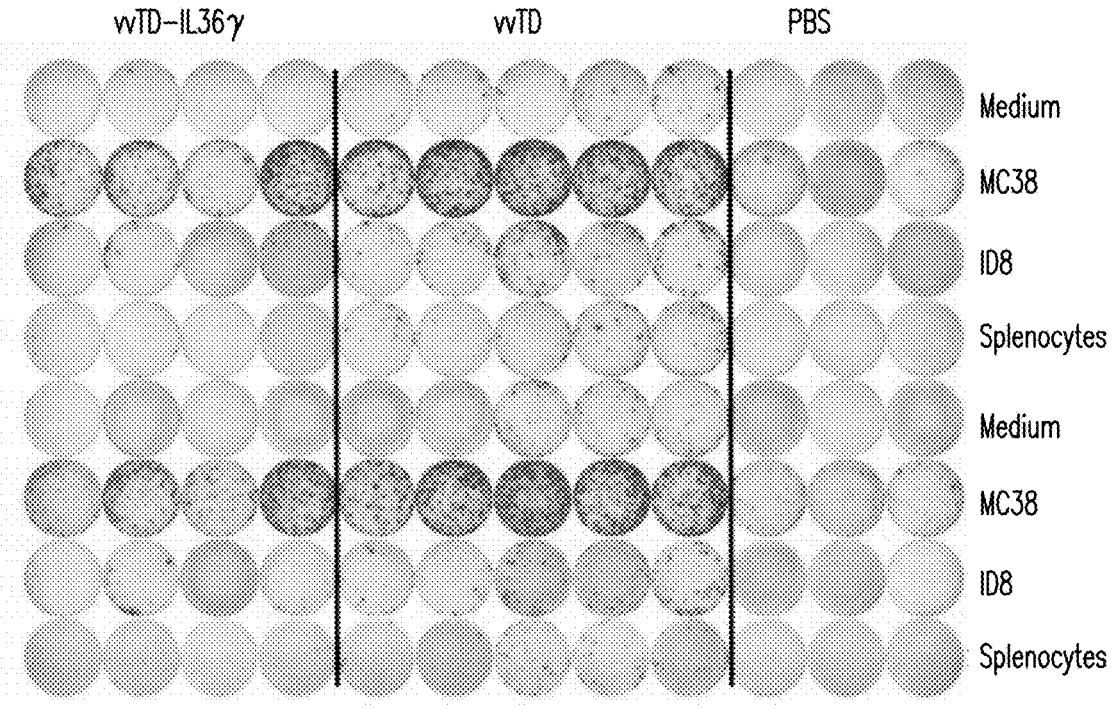
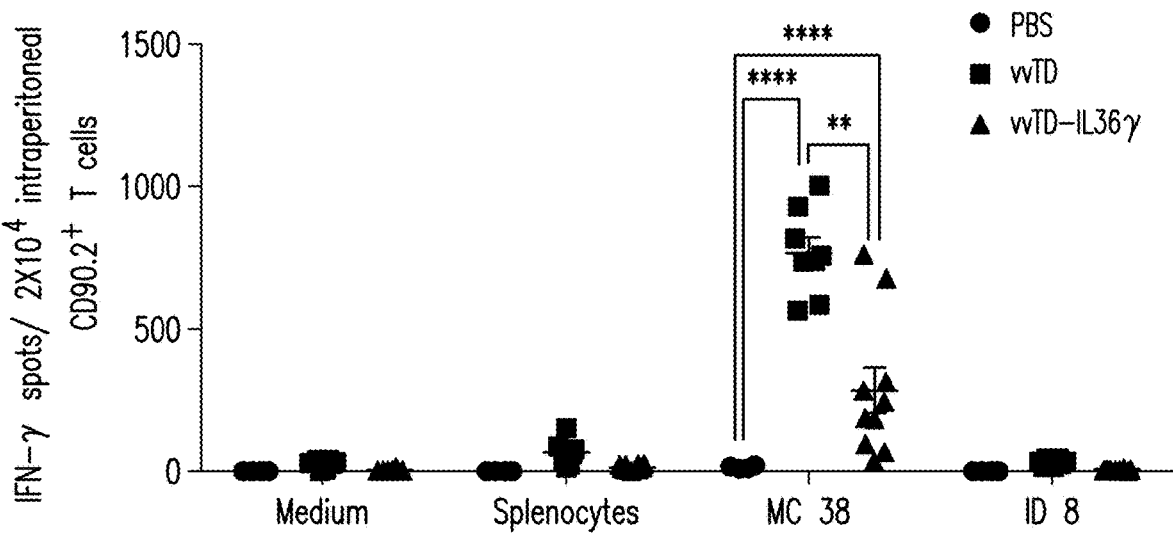
FIG. 11A

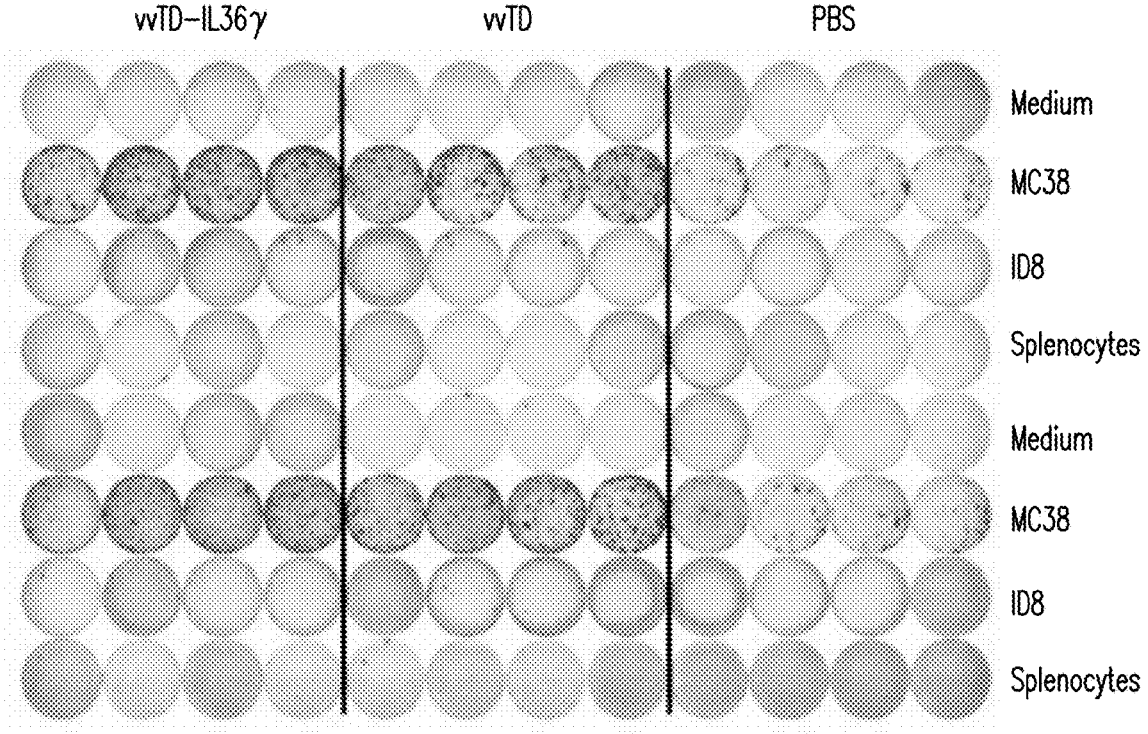
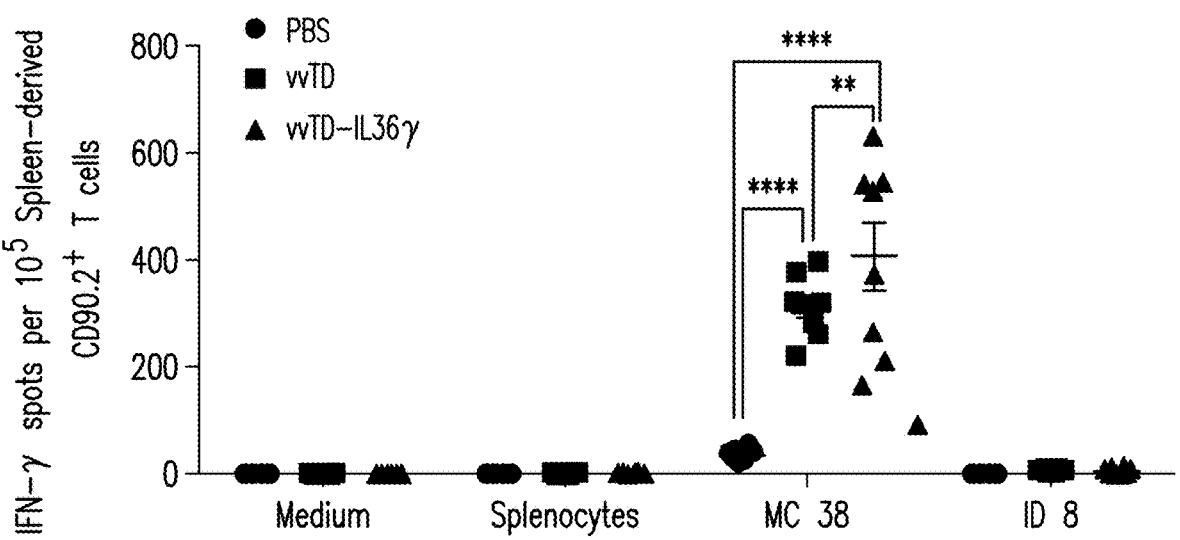
FIG. 11B

SEQUENCE LISTING

<160> NUMBER OF SEQ ID NOS: 4

<210> SEQ ID NO 1

```
<211> LENGTH: 134
<212> TYPE: PRT
<213> ORGANISM: Homo sapiens

<400> SEQUENCE: 1

Met Arg Gly Thr Pro Gly Asp Ala Asp Gly Gly Arg Ala Val Tyr
1               5                   10                  15

Gln Ser Ile Thr Val Ala Val Ile Thr Cys Lys Tyr Pro Glu Ala Leu
            20                  25                  30

Glu Gln Gly Arg Gly Asp Pro Ile Tyr Leu Gly Ile Gln Asn Pro Glu
            35                  40                  45

Met Cys Leu Tyr Cys Glu Lys Val Gly Glu Gln Pro Thr Leu Gln Leu
            50                  55                  60

Lys Glu Gln Lys Ile Met Asp Leu Tyr Gly Gln Pro Glu Pro Val Lys
65                  70                  75                  80

Pro Phe Leu Phe Tyr Arg Ala Lys Thr Gly Arg Thr Ser Thr Leu Glu
                85                  90                  95

Ser Val Ala Phe Pro Asp Trp Phe Ile Ala Ser Ser Lys Arg Asp Gln
                100                 105                 110

Pro Ile Ile Leu Thr Ser Glu Leu Gly Lys Ser Tyr Asn Thr Ala Phe
            115                 120                 125

Glu Leu Asn Ile Asn Asp
            130

<210> SEQ ID NO 2
<211> LENGTH: 402
<212> TYPE: DNA
<213> ORGANISM: Homo sapiens

<400> SEQUENCE: 2
atgcgcggca ccccgggcga tgcggatggc ggcggccgcg cggtgtatca gagcattacc        60
gtggcggtga ttacctgcaa atatccggaa gcgctggaac agggccgcgg cgatccgatt       120
tatctgggca ttcagaaccc ggaaatgtgc ctgtattgcg aaaaagtggg cgaacagccg       180
accctgcagc tgaaagaaca gaaaattatg gatctgtatg gccagccgga accggtgaaa       240
ccgtttctgt tttatcgcgc gaaaaccggc cgcaccagca ccctggaaag cgtggcgttt       300
ccggattggt ttattgcgag cagcaaacgc gatcagccga ttattctgac cagcgaactg       360
ggcaaaagct ataacaccgc gtttgaactg aacattaacg at                          402

<210> SEQ ID NO 3
<211> LENGTH: 169
<212> TYPE: PRT
<213> ORGANISM: Homo sapiens

<400> SEQUENCE: 3

Met Arg Gly Thr Pro Gly Asp Ala Asp Gly Gly Gly Arg Ala Val Tyr
1               5                   10                  15

Gln Ser Met Cys Lys Pro Ile Thr Gly Thr Ile Asn Asp Leu Asn Gln
            20                  25                  30

Gln Val Trp Thr Leu Gln Gly Gln Asn Leu Val Ala Val Pro Arg Ser
            35                  40                  45

Asp Ser Val Thr Pro Val Thr Val Ala Val Ile Thr Cys Lys Tyr Pro
            50                  55                  60

Glu Ala Leu Glu Gln Gly Arg Gly Asp Pro Ile Tyr Leu Gly Ile Gln
65                  70                  75                  80

Asn Pro Glu Met Cys Leu Tyr Cys Glu Lys Val Gly Glu Gln Pro Thr
```

-continued

```
                85                 90                 95

Leu Gln Leu Lys Glu Gln Lys Ile Met Asp Leu Tyr Gly Gln Pro Glu
            100               105               110

Pro Val Lys Pro Phe Leu Phe Tyr Arg Ala Lys Thr Gly Arg Thr Ser
        115               120               125

Thr Leu Glu Ser Val Ala Phe Pro Asp Trp Phe Ile Ala Ser Ser Lys
    130               135               140

Arg Asp Gln Pro Ile Ile Leu Thr Ser Glu Leu Gly Lys Ser Tyr Asn
145               150               155               160

Thr Ala Phe Glu Leu Asn Ile Asn Asp
                165

<210> SEQ ID NO 4
<211> LENGTH: 507
<212> TYPE: DNA
<213> ORGANISM: Homo sapiens

<400> SEQUENCE: 4
atgcgcggca ccccgggcga tgcggatggc ggcggccgcg cggtgtatca gagcatgtgc        60
aaaccgatta ccggcaccat taacgatctg aaccagcagg tgtggaccct gcagggccag       120
aacctggtgg cggtgccgcg cagcgatagc gtgaccccgg tgaccgtggc ggtgattacc       180
tgcaaatatc cggaagcgct ggaacagggc cgcggcgatc cgatttatct gggcattcag       240
aacccggaaa tgtgcctgta ttgcgaaaaa gtgggcgaac agccgaccct gcagctgaaa       300
gaacagaaaa ttatggatct gtatggccag ccggaaccgg tgaaaccgtt tctgttttat       360
cgcgcgaaaa ccggccgcac cagcaccctg gaaagcgtgg cgtttccgga ttggtttatt       420
gcgagcagca aacgcgatca gccgattatt ctgaccagcg aactgggcaa aagctataac       480
accgcgtttg aactgaacat taacgat                                           507
```

IL-36 CYTOKINE EXPRESSING ONCOLYTIC VIRUSES FOR TREATING CANCER

CROSS-REFERENCE TO RELATED APPLICATIONS

This application is a continuation of International Patent Application No. PCT/US20/51467, filed Sep. 18, 2020, which claims priority to U.S. Provisional Patent Application Ser. No. 62/903,346, filed Sep. 20, 2019, the contents of each of which are incorporated by reference in their entirety, and to each of which priority is claimed.

GRANT INFORMATION

This disclosure was made with government support under grant number CA205727 awarded by National Institutes of Health. The government has certain rights in the disclosure.

SEQUENCE LISTINGS

The instant application contains a Sequence Listing, which has been submitted electronically in ASCII format and is hereby incorporated by reference in its entirety. Said ASCII copy, created on Mar. 3, 2022, is named 0723960915SL.txt and is 4,474 bytes in size.

TECHNICAL FIELD

The present disclosure provides interleukin-36 (IL-36) cytokine (e.g., IL-36γ) expressing oncolytic viruses, and compositions comprising thereof. The present disclosure further provides methods of using said oncolytic viruses and compositions for treating cancer, and for improving a subject's responsiveness to an immunomodulatory agent.

BACKGROUND

Immunotherapy, such as immune checkpoint inhibitors, has been used clinically for treating various cancers, such as melanoma, non-small cell lung cancer, renal cell carcinoma, and MSI-high colorectal carcinoma (Ribas et al., *Science* 359, 1350-1355 (2018)). However, only a small portion of patients can benefit from immune checkpoint inhibitor treatment. One reason is that many patients are inherently nonresponsive to immune checkpoint inhibitors, or have obtained drug resistance to immune checkpoint inhibitors during the treatment (Ribas et al., *Science* 359, 1350-1355 (2018)).

Oncolytic virus (OV)-based therapy is a promising cancer therapy (Bartlett et al., *Mol Cancer* 12, 103 (2013); Lichty et al., *Nat Rev Cancer* 14, 559-567 (2014); Lawler et al., *JAMA Oncol* 3, 841-849 (2017)). Oncolytic viruses can induce oncolysis of infected cancer cells and tumor-associated stromal cells, usually in the form of immunogenic cell death. Immunogenic cell death can further induce adaptive antitumor immune responses (Bartlett et al., *Mol Cancer* 12, 103 (2013)). However, oncolytic virotherapy has had limited efficacy in clinical trials.

Thus, there remain needs for methods and compositions for improving the efficacy and potency of OV-based cancer therapy, and for improving patients' responsiveness to immunotherapy.

SUMMARY OF THE INVENTION

The present disclosure provides oncolytic viruses expressing IL-36 cytokines, and compositions comprising thereof. It is based, at least in part, on the discovery that IL-36 cytokine expressing oncolytic viruses improved the anti-tumor effects of the oncolytic viruses in vivo.

In one aspect, the present disclosure provides an oncolytic virus comprising a nucleic acid molecule encoding interleukin-36γ (IL-36γ).

In certain embodiments, the IL-36γ is a human IL-36γ or a mouse IL-36γ. In certain embodiments, the IL-36γ is a recombinant IL-36γ.

In certain embodiments, the nucleic acid molecule is an exogenous nucleic acid molecule. In certain embodiments, the nucleic acid molecule is integrated into the genome of the oncolytic virus. In certain embodiments, the nucleic acid molecule is a DNA molecule.

In certain embodiments, the nucleic acid molecule is operably linked to a promoter.

In certain embodiments, the oncolytic virus is an oncolytic vaccinia virus.

In certain embodiments, the promoter is a vaccine virus promoter. In certain embodiments, the vaccine virus promoter is p7.5 or pSE/L.

In certain embodiments, the oncolytic vaccinia virus lacks the expression of a functional thymidine kinase (TK). In certain embodiments, the oncolytic vaccinia virus comprises a mutation of the J2R gene. In certain embodiments, the nucleic acid molecule is integrated into the locus of the J2R gene. In certain embodiments, the oncolytic vaccinia virus lacks the expression of a functional vaccinia growth factor (VGF). In certain embodiments, the oncolytic vaccinia virus comprises a mutation of the C11R gene.

In certain embodiments, the oncolytic vaccinia virus: (a) lacks the expression of the functional TK; and (b) lacks the expression of the functional VGF.

In certain embodiments, the oncolytic vaccinia virus comprises: (a) the mutation of the J2R gene; and (b) the mutation of the C11R gene.

In certain embodiments, the oncolytic vaccinia virus lacks the expression of a functional serine proteinase inhibitor 1 (SPI-1). In certain embodiments, the oncolytic vaccinia virus comprises a mutation of the B22R gene. In certain embodiments, the oncolytic vaccinia virus lacks the expression of a functional serine proteinase inhibitor 2 (SPI-2). In certain embodiments, the oncolytic vaccinia virus comprises a mutation of the B13R gene.

In certain embodiments, the oncolytic vaccinia virus: (a) lacks the expression of the functional TK; (b) lacks the expression of the functional SPI-2; and (c) lacks the expression of the functional SPI-1.

In certain embodiments, the oncolytic vaccinia virus comprises: (a) the mutation of the J2R gene; (b) the mutation of the B22R gene; and (c) the mutation of the B13R gene.

In certain embodiments, the oncolytic vaccinia virus is a Western Reserve strain.

In another aspect, the present disclosure provides a method of treating a subject having cancer, comprising administering to the subject an oncolytic virus comprising a nucleic acid molecule that encodes IL-36γ.

In certain embodiments, the method improves the anti-cancer adaptive immune response in the subject. In certain embodiments, the method promotes the immunogenicity of a tumor microenvironment of the subject.

In certain embodiments, the cancer is selected from the group consisting of adenocarcinomas, osteosarcomas, cervical carcinomas, melanomas, hepatocellular carcinomas, breast cancers, lung cancers, prostate cancers, ovarian cancers, leukemia, lymphomas, renal carcinomas, pancreatic cancers, gastric cancers, colon cancers, duodenal cancers, glioblastoma multiforme, astrocytomas, sarcomas, and combinations thereof. In certain embodiments, the cancer is selected from the group consisting of pancreatic cancers, colorectal cancers, melanomas, and combinations thereof.

In certain embodiments, the subject is a human subject.

In certain embodiments, the method disclosed herein further comprises administering an immunomodulatory agent to the subject.

In certain embodiments, the immunomodulatory agent is selected from the group consisting of immune checkpoint inhibitors, T cells, dendritic cells, therapeutic antibodies, cancer vaccines, cytokines, *Bacillus* Calmette-Guérin (BCG), and any combinations thereof. In certain embodiments, the immunomodulatory agent is an immune checkpoint inhibitor.

In certain embodiments, the immune checkpoint inhibitor is selected from the group consisting of anti-PD1 antibodies, anti-PD-L1 antibodies, anti-CTLA-4 antibodies, anti-BTLA antibodies, anti-TIM3 antibodies, anti-LAG-3 antibodies, and any combinations thereof.

In another aspect, the present disclosure provides a method for improving a subject's responsiveness to an immunomodulatory agent, comprising administering to the subject the immunomodulatory agent and an oncolytic virus that expresses IL-36γ, wherein the subject has cancer.

In another aspect, the present disclosure provides a pharmaceutical composition comprising an oncolytic virus comprising a nucleic acid molecule that encodes IL-36γ.

In certain embodiments, the pharmaceutical composition further comprises an immunomodulatory agent.

BRIEF DESCRIPTION OF THE DRAWINGS

FIG. 1A depicts three IL-36γ-armed oncolytic VVs, which contained various backbone with deletional mutations of viral genes. FIG. 1B depicts production and secretion of IL-36γ from infected HeLa cells. HeLa cells in 6-well plate were mock-infected or infected with vvTK- or vvTK-IL-36γ, at MOI of about 1.0. At 48-hour post-infection, conditioned media were collected and subjected to Western blot analysis. W: protein markers; lanes 1, 2: vvTK-IL36γ; lane 3: vvTK-; lane 4: mock-infected. Lanes 5 & 6: B16-IL-36γ cells. FIG. 1C depicts viral replication in MC38 cancer cells. Harvested cells were lysed and the cell lysate was tittered using viral plaque assay. FIG. 1D depicts that MC38-luc cells were infected with OVs at MOI of 0.5, then harvested at varying time points. Cell suspensions were stained with 0.4% trypan blue solution and then viable cells were counted under visible light microscopy. FIGS. 1E and 1F depict oncolysis of virus-infected human cancer cells (HepG2 cells and MDA-MB-468 cells). Cancer cells in 96-well culture plates were infected with viruses at MOI of 1.0. Cell viability was then assessed at 24-hour, 36-hour, 48-hour and 72-hour timepoints after infection, with MTS assays.

FIG. 2A depicts tumor burden of mice on days 5 and day 23 as determined by bioluminescence imaging. FIG. 2B depicts long term survival of MC38-luc tumor-bearing mice as Kaplan-Meier survival curves. ***p<0.0001. FIG. 2C provides that on day 140, the previously cured mice with vvTK- or vvTK-IL36γ, along with a group of naïve mice, were challenged with cells of MC38-luc tumor (5.0×10⁵ tumor cells) at the right flank and Lewis lung carcinoma (LLC, with 5.0×10⁵ cells) at the left flank. Tumor formation was observed twice a week until day 40.

FIG. 3A provides that B6 mice were inoculated with 2.0×10⁵ B16 cells on the right flank on day 0 (D0). On day 9, either PBS or OVs at a dose of 5.0×10⁷ pfu/50 μL was injected intratumorally. Tumor growth was monitored twice a week. Death was recorded when mice died naturally, or when mice were sacrificed due to the diameter of tumor reaching 2.0 cm. Long term survival of B16 tumor-bearing mice as Kaplan-Meier survival curves. For the whole experiment, *p<0.0001. For comparison of vvTK- vs vvTK-IL36γ, p=0.024; for vvTD vs vvTD-IL36γ, p=0.002. FIG. 3B provides that mice was inoculated with 1.0×10⁶ panc02-luc cells i.p., and tumor growth was monitored by bioluminescence imaging on day 7 and mice with similar sizes of tumor burden were randomly divided into 3 groups, and treated with PBS, vvTK-, or vvTK-IL36γ (1.0e8 pfu/each mouse). Long term survival of panc02-luc tumor-bearing mice as Kaplan-Meier survival curves. p=0.017, vvTD vs vvTD-IL36γ. For the whole experiment, *p<0.0001.

FIG. 4A provides that ten days post treatment, tumor tissues were collected, fixed and stained for CD3, CD4, CD8, and DAPI. From each group, a representative image is presented. FIG. 4B provides that summary of the percentage of CD3+ T cells, CD3+CD4+ T cells and CD3+CD8+ T cells per area. The statistical significance between groups are indicated in the graphs.

FIG. 5A provides the experimental scheme. The mice treated with vvTK-IL36γ were divided into 4 groups (n=8), and further treated with PBS, anti-CD4 antibody, anti-CD8 antibody, or anti-NK antibody as described in Example 1. The survival of mice was monitored and Kaplan Meier analysis was performed. Results of the survival analysis are shown in FIG. 5B. Statistical analyses: p=0.025 for vvTK-IL-36γ versus vvTK-IL36γ+ anti-CD4; p<0.01 for vvTK-IL-36γ versus vvTK-IL36γ plus anti-CD8; p=0.06 for vvTK-IL36γ versus vvTK-IL36γ plus anti-NK ab treatment. For the whole experiment, p≤0.0001.

FIGS. 6A-6I provide IL-36γ-armed OV promoted antitumor immunity via changing the TME. Mice were inoculated with 5.0×10⁵ MC38-luc cells i. p., and 7 days later, mice with similar sizes of tumor burden were randomly divided into 3 groups, and treated with PBS, or OVs. Six days later, lavage cells were analyzed by FACS. FIG. 6A provides that lymphocytes were gated based on the CD45 expressions in addition to Forward and Side scatters. FIG. 6B depicts IFNγ⁺CD8⁺ T cells. FIG. 6C depicts CD11b⁺GR-1⁺

MDSCs. FIG. 6D depicts TAMs, which were gated as $CD45^+CD11b^+GR\text{-}1^-MHCII^+CD24^-F4/80^+$. FIG. 6E depicts $CD206^+$ TAMs, which were gated as $CD45^+CD11b^+$ $GR\text{-}1^-MHCII^+CD24^-F4/80^+CD206^+$. FIG. 6F depicts DCs, which were gated as $CD45^+CD11b^+GR\text{-}1^-MHCII^+CD24^+$ $F4/80^-$. FIG. 6G depicts naïve $CD8^+$ T cells, which were gated as $CD44^-$ $CD62L^+$ $CD8^+$. FIG. 6H depicts memory-phenotype $CD8^+$ T cells, which were gated as $CD44^+CD8^+$. FIG. 6I depicts effector memory ($CD44^+$ $CD62L^-$) CD8+ T cells. $p<0.01$. $*p<0.001$. $****p<0.0001$.

FIG. 7A depicts representative image of IFNγ ELISPOT assay of $2.0\times10^4$ $CD90.2^+$ T cells isolated from lavage specimens on day 6 post oncolytic virotherapy and co-cultured 1:1 with specific (MC38) and unspecific (medium, ID8, splenocytes) target cells and analysis of ImmunoSpot™ counted spots. FIG. 7B provides that 4-1BB$^+$ memory phenotype $CD44^+CD8^+$ T cells showed enhanced MC38-specific activation assessed by 4-1BB surface expression after co-culture assay with MC38 and unspecific target cells (medium, unloaded splenocytes, ID8 cells). FIG. 7C depicts percentage of 4-1BB$^+$ memory phenotype $CD44^+CD8^+$ T cells, following co-culture assay with $p15E_{604\text{-}611}$ and $B8R_{20\text{-}27}$ loaded splenocytes and $OVA_{257\text{-}264}$ and unloaded splenocytes as unspecific targets, which revealed augmented 4-1BB dependent activation by retroviral peptide $p15E_{604\text{-}611}$ and $B8R_{20\text{-}27}$. FIG. 7D depicts percentage of OX40$^+$ $CD4^+$ T cells per total $CD4^+$ T cells following in vitro co-culture assay with MC38 and unspecific targets as negative controls. $p<0.01$; $*p<0.001$; $****p<0.0001$.

FIGS. 9A-9F provide FACS analysis of immune cells in lavage 6 days post OV therapy. FIG. 9A provides FACS analysis of CD45+ cells. FIG. 9B provides FACS analysis of IFN-γ+CD4+ T cells. FIG. 9C provides FACS analysis of Gr1+CD11b+ MDSCs. FIG. 9D provides FACS analysis of CD24+ F4/80+ TAMs. FIG. 9E provides FACS analysis of CD206+ CD11b+ M2-like TAMs. FIG. 9F provides FACS analysis of CD4+ Foxp3+ Treg.

FIGS. 10A-10F provide analysis of immune cells in lavage specimen on day 6 and day 11 post immunotherapy. FIG. 10A depicts that tumor associated macrophages (TAM), defined as F4/80+ cells per CD45+ CD11b+ cells, were less prevalent in lavage from vvTD-IL36γ-treated animals when compared to parental virus-treated animals. FIG. 10B depicts that percentage of granulocytic myeloid-derived suppressor cells (G-MDSC), marked as CD45+ $CD11b+$ $Ly6G^+Ly6C^{low}$, was highest in sham-treated animals, while no difference in the percentage of monocytic MDSC (M-MDSC), described as CD45+ CD11b+ Ly6G- $Ly6C^{high}$, was seen. FIG. 10C depicts that NK cells, which were marked as CD45+ CD3− NK1.1+ cells, had no difference in existence in lavage specimen on day 6 post immunotherapy. FIGS. 10E and 10F depict that no significant difference in TAM presence nor PMN-MDSC and M-MDSC presence were found on day 11 post therapy. FIG. 10F depicts that NK cells were increased in lavage specimens of vvTD-YFP-IL36γ-treated animals in comparison to sham and parental virus treated animals. $*p<0.05$. $**p<0.01$.

FIGS. 11A-11B provide vvTD-IL36γ induced MC38-spedific $CD8^+$ T cells in the intraperitoneal space vanish after 11 days post oncolytic virotherapy in correspondence with cancer disappearance, while cultivating an enhanced systemic MC38-specific immune response in the spleen. FIG. 11A shows representative image of IFNγ ELISPOT of $2\times10^4$ $CD90.2^+$ T cells isolated from lavage specimens on day 11 post oncolytic virotherapy and co-cultured 1:1 with specific (MC38) and unspecific (medium, ID8, splenocytes) target cells and analysis of ImmunoSpot™ counted spots. FIG. 11A shows representative image of IFN-γ ELISPOT of $10^5$ $CD90.2^+$ T cells isolated from the spleen on day 11 post oncolytic virotherapy and co-cultured 1:1 with specific (MC38) and unspecific (medium, ID8, splenocytes) target cells and analysis of ImmunoSpot™ counted spots. $p<0.01$. $*p<0.001$. $****p<0.0001$.

FIG. 12A provides that immune cells (viable $CD45^+$) in intraperitoneal lavage specimen were increased after paternal and IL36γ expressing virus, while the amounts of lymphocytes (viable $CD45^+$ $CD3^+$) contained in intraperitoneal lavage specimen showed no difference. FIG. 12B provides that the percentage of $CD8^+$ T cells per immune cells was increased, while the amount of $CD4^+$ T cells was decreased with either oncolytic virus treatment. Only NK cells showed a significant increase after IL36γ expressing oncolytic virotherapy. Intermediate expression of PD-1 (FIG. 12C) was higher after parental or IL36γ expressing virus, with no observed change in expression of TIGIT (FIG. 12D) and TIM-3 (FIG. 12E) in the $CD8^+$ population in comparison to PBS. $p<0.01$. $*p<0.001$. $****p<0.0001$.

FIG. 13A provides that B6 mice were inoculated with $2.0\times10^5$ B16 cells on the right flank on day 0 (D0). On day 9, either PBS or OVs at a dose of $5.0\times10^7$ pfu/50 μL was injected intratumorally. Tumor growth was monitored twice a week. Death was recorded when mice died naturally, or when mice were sacrificed due to the diameter of tumor reaching 2.0 cm. Long term survival of B16 tumor-bearing mice as Kaplan-Meier survival curves. For the whole experiment, $*p<0.001$. For comparison of vvTK- vs vvTK-IL36γ, p=0.024; for vvTD vs vvTD-IL36γ, p=0.002. FIG. 13B provides that mice was inoculated with $1.0\times10^6$ panc02-luc cells i.p., and tumor growth was monitored by bioluminescence imaging on day 7 and mice with similar sizes of tumor burden were randomly divided into 3 groups, and treated with PBS, vvTK-, or vvTK-IL36γ (1.0e8 pfu/each mouse). Long term survival of panc02-luc tumor-bearing mice as Kaplan-Meier survival curves. p=0.017, vvTD vs vvTD-IL36γ. For the whole experiment, *p<0.001. FIG. 13C provides tumor sizes of subcutaneous MC38-luc tumors treated with IL-36γ-OVs or PBS. B6 mice were inoculated with $2.0\times10^5$ MC38-luc cells on the right flank on day 0 (D0). When tumor size reaches to 5×5 mm (~day 12), either PBS or OVs at a dose of $5.0\times10^7$ pfu/50 μL was injected intratumorally. Tumor growth was monitored twice a week. *p<0.001. FIG. 13D provides long-term survival analysis of subcutaneous MC38-luc tumor-bearing mice after indicated treatments as shown in FIG. 3C. *p<0.001; ns, not significant. Data were representative of two independent experiments. n=6–10 for each group.

DETAILED DESCRIPTION

Figures 1A, 1B:
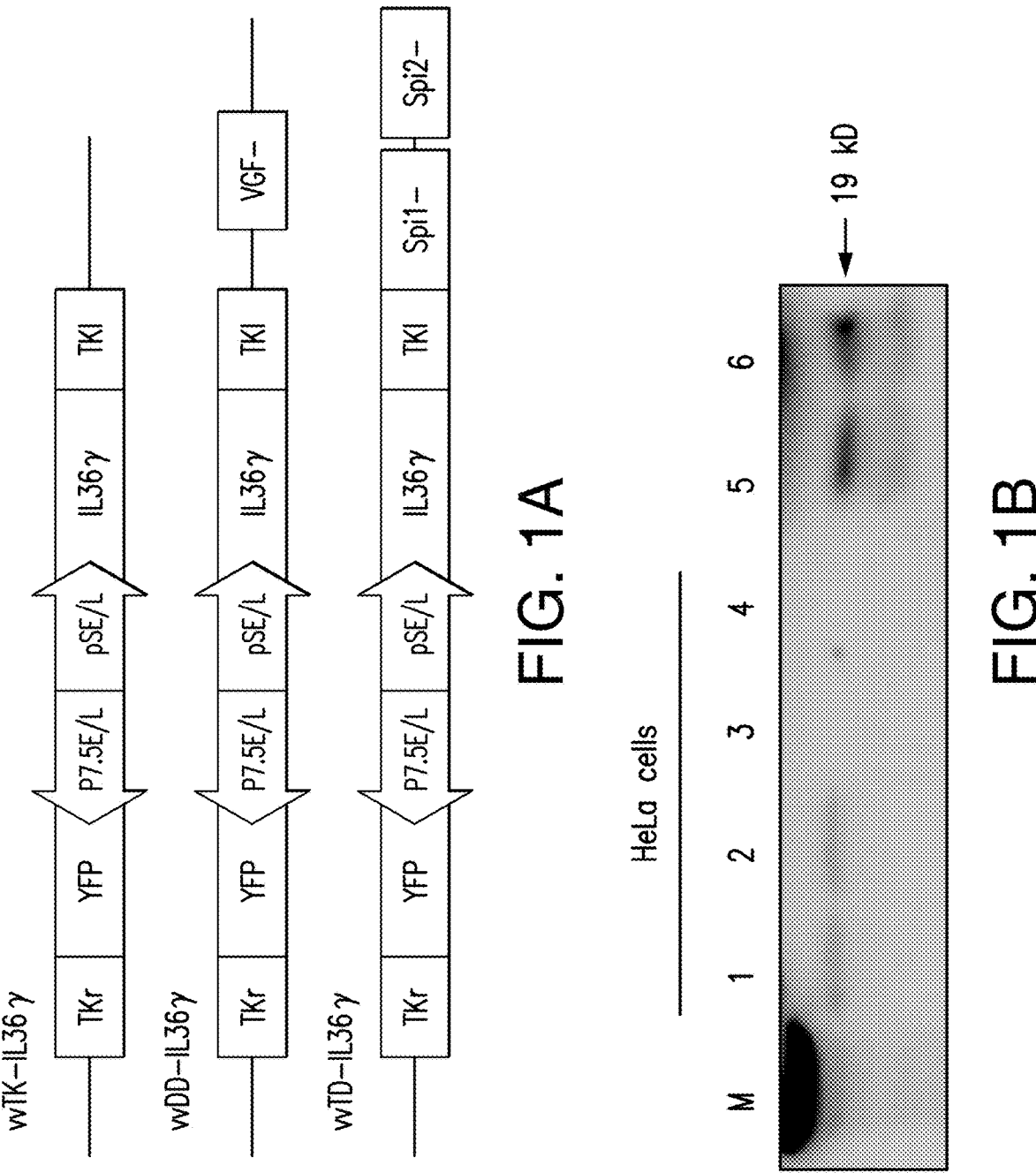
FIGS. 1A-1F provide that IL-36γ-armed vaccinia viruses (VVs) were oncolytic viruses (OVs) and produced recombinant cytokine IL-36γ in infected cancer cells in vitro.

Non-limiting embodiments of the present disclosure are described by the present specification and Examples.

For purposes of clarity of disclosure and not by way of limitation, the detailed description is divided into the following subsections:

1. Definitions;
2. Oncolytic Viruses Expressing IL-36γ;
3. Pharmaceutical Compositions;
4. Methods of Treatment; and
5. Kits.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of", and "consisting essentially of," the embodiments or elements presented herein, whether explicitly set forth or not.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "oncolytic virus" or "OV" refers to a virus capable of selectively replicating in a cancer cell, and slowing the growth or inducing the death of the cancer cell, either in vitro or in vivo, while having no or minimal effect on normal cells. In certain embodiments, the oncolytic viruses spread within a tumor without causing damages to non-cancerous tissues. In certain embodiments, the oncolytic viruses do not replicate or replicate at a reduced speed in non-cancer cells as compared to in cancer cells. Non-limiting exemplary oncolytic viruses include Coxsackieviruses, Maraba viruses (rhabdovirus), Parvoviruses, Seneca Valley viruses, vesicular stomatitis viruses (VSVs), Newcastle disease viruses (NDVs), retroviruses, reoviruses, measles viruses, Sindbis viruses, influenza viruses, herpes simplex viruses (HSVs), Sendai viruses, vaccinia viruses (VVs), and adenoviruses, and variants thereof.

As used herein, the term "vaccinia virus" or "VV" refers to an enveloped DNA virus from the poxvirus family. In certain embodiments, the VV comprises a linear, double-stranded DNA genome of about 200 kb. Non-limiting examples of vaccinia virus strains include strains of, derived from, or modified forms of Western Reserve (WR) strain, Tashkent strain, Lister strain (also known as Elstree), Dryvax strain (also known as Wyeth strain), IHD-J strain, and IHD-W strain, Brighton strain, Ankara strain, modified vaccinia Ankara (MVA) strain, Dairen strains (e.g., Dairen I strain (DIs)), LIPV strain, lister clone 16m8 (LC16m8) strain, LC16MO strain, LIVP strain, WR 65-16 strain, Connaught strain, New York City Board of Health (NYCBH) strain, EM63 strain, ACAM2000™ strain, CV-1 strain, Paris strain, Copenhagen (Cop) strain, Bern strain, and the Tian Tan (VTT) strain.

The term "nucleic acid molecule" and "nucleotide sequence," as used herein, refers to a single or double-stranded covalently-linked sequence of nucleotides in which the 3' and 5' ends on each nucleotide are joined by phosphodiester bonds. The nucleic acid molecule can include deoxyribonucleotide bases or ribonucleotide bases, and can be manufactured synthetically in vitro or isolated from natural sources.

The terms "polypeptide," "peptide," "amino acid sequence" and "protein," used interchangeably herein, refer to a molecule formed from the linking of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis or enzymatic synthesis. The terms can apply to amino acid polymers in which one or more amino acid residue is an artificial chemical mimetic of a corresponding naturally occurring amino acid, as well as to naturally occurring amino acid polymers and non-naturally occurring amino acid polymers.

As used herein, the term "mutation" refers to a mutation in an amino acid sequence or in a nucleic acid sequence. In certain embodiments, a mutation in an amino acid sequence can be a substitution (replacement), an insertion (addition), or a deletion (truncation) of at least one amino acid in the amino acid sequence. In certain embodiments, a mutation in a nucleic acid sequence can be a substitution (replacement), an insertion (addition), or a deletion (truncation) of at least nucleotide of the nucleic acid sequence.

The term "endogenous," as used herein, refers to a nucleic acid molecule or polypeptide that is normally expressed in a cell or tissue.

The term "exogenous," as used herein, refers to a nucleic acid molecule or polypeptide that is not endogenously present in a cell. The term "exogenous" would therefore encompass any recombinant nucleic acid molecule or polypeptide expressed in a cell, such as foreign, heterologous, and over-expressed nucleic acid molecules and polypeptides. By "exogenous" nucleic acid is meant a nucleic acid not present in a native wild-type cell; for example, an exogenous nucleic acid may vary from an endogenous counterpart by sequence, by position/location, or both. For clarity, an exogenous nucleic acid may have the same or different sequence relative to its native endogenous counterpart; it may be introduced by genetic engineering into the cell itself or a progenitor thereof, and may optionally be linked to alternative control sequences, such as a non-native promoter or secretory sequence.

By "increase" is meant to alter positively by at least about 5%. An alteration can be an increase of about 5%, about 10%, about 25%, about 30%, about 50%, about 75%, about 100% or more.

By "reduce" is meant to alter negatively by at least about 5%. An alteration can be a decrease of about 5%, about 10%, about 25%, about 30%, about 50%, about 75% or more, even by about 100%.

As used herein, "a functional fragment" of a molecule or polypeptide includes a fragment of the molecule or polypeptide that retains at least about 80%, at least about 85%, at least about 90%, at least about 95%, or at least about 100% of the primary function of the molecule or polypeptide.

As used herein, the term "substantially identical" or "substantially homologous" refers to a polypeptide or a nucleic acid molecule exhibiting at least about 50% identical or homologous to a reference amino acid sequence (for example, any of the amino acid sequences described herein) or a reference nucleic acid sequence (for example, any of the nucleic acid sequences described herein). In certain embodiments, such a sequence is at least about 60%, at least about 65%, at least about 70%, at least about 75%, at least about 80%, at least about 85%, at least about 90%, at least about 95%, at least about 99%, or at least about 100% identical or homologous to the amino acid sequence or the nucleic acid sequence used for comparison.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

As used herein, the term "therapeutically effective amount" or "effective amount" refers to an amount of an oncolytic virus composition that is sufficient to reduce, inhibit, or abrogate tumor cell growth, in vitro or in vivo. In certain embodiments, the reduction, inhibition, or abrogation of tumor cell growth may be the result of necrosis, apoptosis, or an immune response. The amount of an oncolytic virus composition that is therapeutically effective or effective may vary depending on the context. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more sign or symptoms, diminishment of extent of disease, stabilized (i.e., not worsening) state of disease, prevention of disease, delay or slowing of disease progression, and/or amelioration or palliation of the disease state. The decrease can be a 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

"In combination with," as used herein, means that an oncolytic virus disclosed herein, and one or more agents, e.g., an immunomodulatory agent, are administered to a subject as part of a treatment regimen or plan.

2. Oncolytic Viruses Expressing IL-36

The present disclosure provides oncolytic viruses expressing an interleukin-36 (IL-36) cytokine. In certain embodiments, the oncolytic virus includes a nucleic acid molecule encoding the IL-36 cytokine. In certain embodiments, the nucleic acid molecule is an exogenous nucleic acid molecule. In certain embodiments, the nucleic acid molecule is integrated into the genome of the oncolytic virus.

2.1 IL-36 Cytokines

IL-36 cytokines are members of IL-1 cytokine family, which plays major roles in initiating and promoting inflammation. In certain embodiments, the IL-36 cytokines are IL-36 receptor agonists that can activate IL-36 receptor ("IL-36R") signaling. Non-limiting examples of IL-36 receptor agonists that can be used with the presently disclosed subject matter include IL-36α, IL-36β, and IL-36γ. In certain embodiments, the oncolytic virus disclosed herein includes a nucleic acid molecule encoding an IL-36 cytokine selected from IL-36α, IL-36β, IL-36γ, and combinations thereof. In certain embodiments, the nucleic acid molecule is an exogenous nucleic acid molecule.

In certain embodiments, the oncolytic virus disclosed herein includes a nucleic acid molecule encoding IL-36γ or a functional fragment thereof. In certain embodiments, the nucleic acid molecule encodes a human IL-36γ or a functional fragment thereof. In certain embodiments, the human IL-36γ has an amino acid sequence that is at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homologous or identical to the amino acid sequence set forth in GenBank/NCBI database accession no. NP_001265497.1, or NP_062564.1. In certain embodiments, the nucleic acid molecule encoding the human IL-36γ may contain substitutions (e.g., conservative substitutions), insertions, or deletions relative to the amino acid sequence set forth in GenBank/NCBI database accession no. NP_001265497.1, or NP_062564.1, that do not significantly alter the function or activity of the human IL-36γ.

In certain embodiments, the human IL-36γ polypeptide comprises or consists of an amino acid sequence that is at least about 85%, about 90%, about 95%, about 96%, about 97%, about 98%, about 99% or 100% homologous or identical to the amino acid sequence set forth in SEQ ID NO: 1, which is provided below.

(SEQ ID NO: 1)
```
MRGTPGDADGGGRAVYQSITVAVITCKYPEALEQGRGDPI

YLGIQNPEMCLYCEKVGEQPTLQLKEQKIMDLYGQPEPVK

PFLFYRAKTGRTSTLESVAFPDWFIASSKRDQPIILTSEL

GKSYNTAFELNIND
```

An exemplary nucleic acid sequence encoding the amino acid sequence of SEQ ID NO: 1 is set forth in SEQ ID NO: 2, which is provided below.

(SEQ ID NO: 2)
```
atgcgcggcaccccgggcgatgcggatggc ggcggccgcgcggtgtatcagagcattacc gtggcggtgattacctgcaaatatccggaa gcgctggaacagggccgcggcgatccgatt tatctgggcattcagaacccggaaatgtgc ctgtattgcgaaaaagtgggcgaacagccg accctgcagctgaaagaacagaaaattatg gatctgtatggccagccggaaccggtgaaa ccgtttctgttttatcgcgcgaaaaccggc cgcaccagcaccctggaaagcgtggcgttt ccggattggtttattgcgagcagcaaacgc gatcagccgattattctgaccagcgaactg ggcaaaagctataacaccgcgtttgaactg aacattaacgat
```

In certain embodiments, the human IL-36γ polypeptide comprises or consists of an amino acid sequence that is at least about 85%, about 90%, about 95%, about 96%, about 97%, about 98%, about 99% or 100% homologous or identical to the amino acid sequence set forth in SEQ ID NO: 3, which is provided below.

(SEQ ID NO: 3)
```
MRGTPGDADGGGRAVYQSMCKPITGTINDLNQQVWTLQGQ

NLVAVPRSDSVTPVTVAVITCKYPEALEQGRGDPIYLGIQ

NPEMCLYCEKVGEQPTLQLKEQKIMDLYGQPEPVKPFLFY

RAKTGRTSTLESVAFPDWFIASSKRDQPIILTSELGKSYN

TAFELNIND
```

An exemplary nucleic acid sequence encoding the amino acid sequence of SEQ ID NO: 3 is set forth in SEQ ID NO: 4, which is provided below.

(SEQ ID NO: 4)
```
atgcgcggcaccccgggcgatgcggatggc ggcggccgcgcggtgtatcagagcatgtgc
```

-continued
```
aaaccgattaccggcaccattaacgatctg aaccagcaggtgtggaccctgcagggccag aacctggtggcggtgccgcgcagcgatagc gtgacccecggtgaccgtggcggtgattacc tgcaaatatccggaagcgctggaacagggc cgcggcgatccgatttatctgggcattcag aacccggaaatgtgcctgtattgcgaaaaa gtgggcgaacagccgaccctgcagctgaaa gaacagaaaattatggatctgtatggccag ccggaaccggtgaaaccgtttctgttttat cgcgcgaaaaccggccgcaccagcaccctg gaaagcgtggcgtttccggattggtttatt gcgagcagcaaacgcgatcagccgattatt ctgaccagcgaactgggcaaaagctataac accgcgtttgaactgaacattaacgat
```

In certain embodiments, the nucleic acid molecule encodes a mouse, a rat, a dog, or a chimpanzee IL-36γ. In certain embodiments, the mouse, the dog, the rat, or the chimpanzee IL-36γ has an amino acid sequence that is at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homologous or identical to the amino acid sequence set forth in GenBank/ NCBI database accession no. NP_705731.2 (mouse), XP_008759827.1 (rat), XP_017447462.1 (rat), XP_022260442.1 (dog), XP_005630506.1 (dog), XP_005630508.1 (dog), XP_024783449.1 (chimpanzee), XP_024783450.1 (chimpanzee), or XP_003804550.1 (chimpanzee). In certain embodiments, the mouse, the dog, the rat, or the chimpanzee IL-36γ may contain substitutions (e.g., conservative substitutions), insertions, or deletions relative to the amino acid sequence set forth in GenBank/ NCBI database accession no. NP_705731.2 (mouse), XP_008759827.1 (rat), XP_017447462.1 (rat), XP_022260442.1 (dog), XP_005630506.1 (dog), XP_005630508.1 (dog), XP_024783449.1 (chimpanzee), XP_024783450.1 (chimpanzee), or XP_003804550.1 (chimpanzee), that do not significantly alter the function or activity of the mouse, the dog, the rat, or the chimpanzee IL-36γ.

In certain embodiments, conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. Amino acids can also be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. In certain embodiments, no more than one, no more than two, no more than three, no more than four, no more than five residues within a specified sequence are altered. Exemplary conservative amino acid substitutions are shown in Table 1 below.

TABLE 1

| Original Residue | Exemplary Conservative Amino Acid Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gin (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid molecule encoding an IL-36 cytokine can be a DNA molecule, an RNA molecule, or a cDNA molecule to conform to the nucleic acid of the oncolytic viral genome into which it is integrated.

2.2 Oncolytic Viruses

Any suitable oncolytic viruses can be used with the presently disclosed subject matter. Non-limited examples of oncolytic viruses that can be used with the presently disclosed subject matter include Coxsackieviruses, Maraba viruses (rhabdovirus), Parvoviruses, Seneca Valley viruses, vesicular stomatitis viruses (VSVs), Newcastle disease viruses (NDVs), retroviruses, reoviruses, measles viruses, Sindbis viruses, influenza viruses, herpes simplex viruses (HSVs), Sendai viruses, vaccinia viruses (VVs), and adenoviruses, and variants thereof.

In certain embodiments, the oncolytic virus disclosed herein is an oncolytic vaccinia virus. Any suitable strains of vaccinia viruses can be used with the presently disclosed subject matter. Non-limiting examples of vaccinia virus strains can be used with the presently disclosed subject matter include strains of, derived from, or modified forms of Western Reserve (WR) strain, Tashkent strain, Lister strain (also known as Elstree), Dryvax strain (also known as Wyeth strain), IHD-J strain, and IHD-W strain, Brighton strain, Ankara strain, modified vaccinia Ankara (MVA) strain, Dairen strain (e.g., Dairen I strain (DIs)), LIPV strain, lister clone 16m8 (LC16m8) strain, LC16MO strain, LIVP strain, WR 65-16 strain, Connaught strain, New York City Board of Health (NYCBH) strain, EM63 strain, ACAM2000™ strain, CV-1 strain, Paris strain, Copenhagen (Cop) strain, Bern strain, and the Tian Tan (VTT) strain. In certain embodiments, the oncolytic vaccinia virus disclosed herein is a Western Reserve strain.

In certain embodiments, the nucleic acid molecule encoding an IL-36 cytokine is integrated into the genome of the oncolytic virus, where the expression of the nucleic acid molecule is operably linked to a promoter that is active or activatable in an oncolytic virus infected cell, for example, a promoter of the oncolytic virus. As used herein, "operably linked" means that a promoter is in a correct functional location and/or orientation in relation to a nucleic acid locus to control transcriptional initiation and/or expression of that locus.

In certain embodiments, the promoter is a vaccinia virus promoter. In certain embodiments, the vaccinia virus promoter is a synthetic vaccinia promoter. In certain embodiments, the vaccinia virus promoter is a p7.5 promoter, which is a classical early-late promoter (Cochran et al., J. Virol. (1985); 54:30-37, the contents of which are incorporated by reference in its entirety). In certain embodiments, the vaccinia virus promoter is a synthetic promoter (pSE/L) that has been used to direct strong early as well as late gene expression (Chakrabarti et al., Biotechniques (1997); 23:1094-1097, the contents of which are incorporated by reference in its entirety).

In certain embodiments, the oncolytic vaccinia virus disclosed herein lacks the expression of a functional thymidine kinase (TK). TK is encoded by the J2R gene (also known as tk gene), and forms part of the salvage pathway for pyrimidine deoxyribonucleotide synthesis. In certain embodiments, the oncolytic vaccinia virus includes a mutation of the J2R gene. In certain embodiments, the mutation of the J2R gene can be a deletion, a substitution, and/or an insertion of at least one nucleotide of the J2R gene nucleic acid sequence. In certain embodiments, the mutation of the J2R gene includes an insertion of a nucleic acid molecule into the locus of the J2R gene. In certain embodiments, the nucleic acid molecule is an exogenous nucleic acid molecule. In certain embodiments, the nucleic acid molecule encodes an IL-36 cytokine (e.g., IL-36 cytokines disclosed in Section 5.2.1).

In certain embodiments, the oncolytic vaccinia virus disclosed herein lacks the expression of a functional vaccinia growth factor (VGF). VGF is encoded by the C11R gene (also known as vgf gene), and functions by stimulating cellular proliferation around infected cells. In certain embodiments, the oncolytic vaccinia virus includes a mutation in the C11R gene. In certain embodiments, the mutation of the C11R gene can be a deletion, a substitution, and/or an insertion of at least one nucleotide of the C11R gene nucleic acid sequence.

In certain embodiments, the oncolytic vaccinia virus disclosed herein lacks the expression of a functional serine proteinase inhibitor 1 (SPI-1). SPI-1 is encoded by the B22R gene (also known as spi-1 gene), and functions by stimulating cellular proliferation around infected cells. In certain embodiments, the oncolytic vaccinia virus includes a mutation in the B22R gene. In certain embodiments, the mutation of the B22R gene can be a deletion, a substitution, and/or an insertion of at least one nucleotide of the B22R gene nucleic acid sequence.

In certain embodiments, the oncolytic vaccinia virus disclosed herein lacks the expression of a functional serine proteinase inhibitor 2 (SPI-2). SPI-2 is encoded by the B13R gene (also known as spi-2 gene), and functions by stimulating cellular proliferation around infected cells. In certain embodiments, the oncolytic vaccinia virus includes a mutation in the B13R gene. In certain embodiments, the mutation of the B13R gene can be a deletion, a substitution, and/or an insertion of at least one nucleotide of the B13R gene nucleic acid sequence.

In certain embodiments, a mutation in a gene (e.g., the J2R gene, the C11R gene, the B22R gene, the B13R gene) is an inactivating mutation, in which the expression of the gene is significantly decreased, or the product encoded by the gene (e.g., TK, VGF, SPI-1, SPI-2) is rendered nonfunctional, or its ability to function is significantly decreased.

In certain embodiments, the oncolytic vaccinia virus disclosed herein comprises: (a) a nucleic acid molecule encoding an IL-36 cytokine, and (b) a mutation is selected from a group consisting of a mutation of the J2R gene, a mutation of the C11R gene, a mutation of the B22R gene, a mutation of the B13R gene, and combinations thereof.

In certain embodiments, the IL-36 cytokine expressing oncolytic vaccinia virus disclosed herein lacks the expression of a functional TK. In certain embodiments, the IL-36 cytokine expressing oncolytic vaccinia virus disclosed herein comprises a mutation of the J2R gene.

In certain embodiments, the IL-36 cytokine expressing oncolytic vaccinia virus disclosed herein lacks the expressions of a functional TK and a functional VGF. In certain embodiments, the IL-36 cytokine expressing oncolytic vaccinia virus disclosed herein comprises a mutation of the J2R gene, and a mutation of the C11R gene In certain embodiments, the IL-36 cytokine expressing oncolytic vaccinia virus disclosed herein lacks the expressions of a functional TK, a functional SPI-1, and a functional SPI-2. In certain embodiments, the IL-36 cytokine expressing oncolytic vaccinia virus disclosed herein comprises a mutation of the J2R gene, a mutation of the B22R gene, and a mutation of the B13R gene.

3. Pharmaceutical Compositions

The present disclosure further provides pharmaceutical compositions that include an oncolytic virus that expresses an IL-36 cytokine or a functional fragment thereof. For example, but not by way of limitation, the methods can include administering to the subject an oncolytic virus that comprises a nucleic acid that encodes an IL-36γ cytokine, e.g., a human IL-36 cytokine, or a functional fragment thereof. Additional non-limiting examples of said oncolytic viruses are disclosed in Section 2. In certain embodiments, the pharmaceutical composition includes an effective amount of the oncolytic virus. In certain embodiments, the pharmaceutical composition can be prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof.

In certain embodiments, the pharmaceutical composition described herein further includes a pharmaceutically acceptable carrier, e.g., an excipient. In certain embodiments, the pharmaceutically acceptable carrier includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically acceptable carriers include gels, bioadsorbable matrix materials, implantation elements containing the oncolytic virus, and any other suitable vehicle, delivery, or dispensing means or material.

In certain embodiments, the pharmaceutically acceptable carrier can be a buffering agent. Non-limiting examples of suitable buffering agents can include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide other calcium salts, and combinations thereof.

In certain embodiments, the oncolytic virus disclosed herein can be propagated in suitable host cells, isolated from host cells, and stored in conditions that promotes stability and integrity of the virus, such that loss of infectivity over time is minimized. In certain embodiments, the oncolytic virus disclosed herein can be stored by freezing or drying, such as by lyophilization. In certain embodiments, prior to administration, the stored oncolytic virus can be reconstituted (if dried for storage) and diluted in a pharmaceutically acceptable carrier for administration.

In certain embodiments, the pharmaceutical composition disclosed herein can further include an immunomodulatory agent (e.g., the immunomodulatory agent disclosed in Section 4.1). In certain embodiments, the pharmaceutical compositions disclosed herein can be provided systemically or directly to a subject for treating and/or preventing a cancer. In certain embodiments, the presently disclosed oncolytic viruses or pharmaceutical compositions are directly injected into an organ of interest (e.g., an organ affected by a cancer). Alternatively, the presently disclosed oncolytic viruses or pharmaceutical compositions are provided indirectly to the organ of interest, for example, by administration into the circulatory system (e.g., the tumor vasculature). When administering a therapeutic composition of the presently disclosed subject matter (e.g., a pharmaceutical composition comprising a presently disclosed oncolytic virus), it can be formulated in a unit dosage injectable form (solution, suspension, emulsion).

4. Methods of Treatment

The present disclosure provides methods of treating a subject having cancer. In certain embodiments, the methods include administering to the subject an oncolytic virus that expresses an IL-36 cytokine or a functional fragment thereof. For example, but not by way of limitation, the methods can include administering to the subject an oncolytic virus that comprises a nucleic acid that encodes an IL-36γ cytokine, e.g., a human IL-36 cytokine, or a functional fragment thereof. Additional non-limiting examples of said oncolytic viruses are disclosed in Section 2.

In certain embodiments, the method disclosed herein reduces aggregated cancer cell mass, reduces cancer cell growth rate, reduces cancer cell proliferation, reduces tumor mass, reduces tumor volume, reduces tumor weight, reduces tumor cell proliferation, reduces tumor growth rate, and/or reduces tumor metastasis in the subject.

In certain embodiments, the method disclosed herein improves the anti-cancer adaptive immune response in the subject. In certain embodiments, the improved anti-cancer adaptive immune response is dependent on the presence and levels of CD4$^+$ and CD8$^+$ T cells in the tumor or tumor microenvironment. In certain embodiments, the method disclosed herein improves adaptive T cell-mediated immune responses.

In certain embodiments, the method disclosed herein modulates a tumor microenvironment. Tumor microenvironment is the environment surrounding a tumor. A tumor microenvironment includes extracellular matrix (ECM), fibroblasts, neuroendocrine (NE) cells, adipose cells, immune, signaling molecules, and the blood and lymphatic vascular networks. Cellular interactions, crosstalks between cancer and immune cells, and interplays between cells and soluble factors (such as cytokines) in the tumor microenvironment determines a subject's immune response to tumor cells. In certain embodiments, the method disclosed herein modifies the tumor microenvironment. In certain embodiments, the method disclosed herein promotes the immunogenicity of the tumor microenvironment. As used herein, the term "immunogenicity" refers to the ability to induce an immune response against cancer, e.g., cancer cells, tumor cells.

In certain embodiments, the method disclosed herein increases the levels of lymphocytes and/or dendritic cells in the tumor or the tumor microenvironment. In certain embodiments, the method disclosed herein does not increase the level of myeloid-derived suppressor cells or M2 type tumor-associated macrophages in the tumor or the tumor microenvironment. In certain embodiments, the method disclosed herein increases the level of T cells in the tumor or the tumor microenvironment. In certain embodiments, the T cells are selected from the group consisting of tumor antigen-specific CD4$^+$ T cells, tumor antigen-specific CD8$^+$ T cells, viral antigen-specific CD4$^+$ T cells, viral antigen-specific CD8$^+$ T cells, and combinations thereof.

Methods disclosed herein can be used for treating any suitable cancers. Non-limiting examples of cancers that can be treated by methods disclosed herein include adenocarcinomas, osteosarcomas, cervical carcinomas, melanomas, hepatocellular carcinomas, breast cancers, lung cancers, prostate cancers, ovarian cancers, leukemias, lymphomas, renal carcinomas, pancreatic cancers, gastric cancers, colon cancers, duodenal cancers, glioblastoma multiforme, astrocytomas, sarcomas, and combinations thereof. In certain embodiments, the method disclosed herein can be used for treating pancreatic cancer, colorectal cancer, melanoma, or a combination thereof.

In certain embodiments, the subject is a human subject. In certain embodiments, the subject is a non-human subject, such as, but not limited to, a non-primate, a dog, a cat, a horse, a rabbit, a mice, a rat, a guinea pig, a fowl, a cow, a goat, or a sheep.

In certain embodiments, the method disclosed herein includes administering the oncolytic virus to the subject in an amount of between about between about 10$^5$ and 10$^{10}$ plaque forming units (PFU). In certain embodiments, the method disclosed herein comprises administering to the subject the oncolytic virus in a single dose, or in multiple doses. In certain embodiments, where the oncolytic virus is administered to the subject in multiple doses, the doses can be administered sequentially, e.g., at daily, weekly, or monthly intervals, or in response to a specific need of the subject.

In certain embodiments, the method disclosed herein comprises administering to the subject a pharmaceutical composition comprising the oncolytic virus disclosed herein (e.g., pharmaceutical compositions disclosed in Section 3).

Any suitable methods of administration can be used with the presently disclosed subject matter for administering the oncolytic virus to the subject having cancer. In certain embodiments, the oncolytic virus disclosed herein is administered systemically. Alternatively or additionally, the oncolytic virus disclosed herein is administered by injection at the site of the cancer, e.g., tumor site. For example, and not by way of limitation, the route of administration can be inhalation, intranasal, intravenous, intraarterial, intrathecal, intratumoral, intraperitoneal, intramuscular, subcutaneous, topical, intradermal, local regional, oral administration, or a combination thereof. In certain embodiments, the oncolytic virus disclosed herein is administered to the subject from a source implanted in the subject. In certain embodiments, the oncolytic virus disclosed herein is administered to the subject by continuous infusion over a selected period of time. In certain embodiments, the oncolytic virus disclosed herein can be administered directly to a tumor site, e.g., via direct intratumoral injection.

4.1 Combinatorial Therapy of Immunotherapy and Oncolytic Viruses

The present disclosure further provides methods for improving a subject's responsiveness to an immunomodulatory agent, comprising administering to the subject the immunomodulatory agent and an oncolytic virus expressing an IL-36 cytokine (e.g., oncolytic viruses disclosed in Section 2), wherein the subject has cancer. For example, but not by way of limitation, a method for improving a subject's responsiveness to an immunomodulatory agent can include administering an oncolytic virus that comprises a nucleic acid that encodes an IL-36γ cytokine, e.g., a human IL-36 cytokine, or a functional fragment thereof with an immunomodulatory agent, wherein the subject has cancer.

The present disclosure also provides methods of treating a subject having a cancer, including administering to the subject an oncolytic virus that expresses an IL-36 cytokine (e.g., oncolytic viruses disclosed in Section 2), and an immunomodulatory agent. For example, but not by way of limitation, an oncolytic virus that comprises a nucleic acid that encodes an IL-36γ cytokine, e.g., a human IL-36 cytokine, or a functional fragment thereof can be administered in combination with an immunomodulatory agent to treat a subject that has cancer.

Any suitable immunomodulatory agent that targets components of the immune system to fight cancer can be used with the presently disclosed methods. Non-limiting examples of immunomodulatory agents include immune checkpoint inhibitors, T cells, dendritic cells, therapeutic antibodies (e.g., anti-CD33 antibodies, anti-CD11b antibodies), cancer vaccines, cytokines (e.g., IL-12, GM-CSF, IL-2, IFNβ, IFNγ, MIP-1, MCP-1, IL-8), *Bacillus* Calmette-Guérin (BCG), and any combinations thereof. In certain embodiments, the immunomodulatory agent is an immune checkpoint inhibitor. In certain embodiments, the immune checkpoint inhibitor is selected from anti-PD1 antibodies, anti-PD-L1 antibodies, anti-CTLA-4 antibodies, anti-BTLA antibodies, anti-TIM3 antibodies, anti-LAG-3 antibodies, and any combinations thereof. Non-limiting examples of anti-PD1 antibodies include pembrolizumab (KEYTRUDA®), nivolumab (OPDIVO®), cemiplimab (LIBTAYO®), and combinations thereof. Non-limiting examples of anti-PD-L1 antibodies include atezolizumab (TECENTRIQ®), avelumab (BAVENCIO®), durvalumab (IMFINZI®), and combinations thereof. Non-limiting examples of anti-CTL4 antibodies include ipilimumab (YERVOY®).

In certain embodiments, the oncolytic virus and the immunomodulatory agent can be administered to the subject as part of a treatment regimen. In certain embodiments, the oncolytic virus and the immunomodulatory agent can be administered concurrently to the subject. In certain embodiments, the oncolytic virus and the immunomodulatory agent can be administered at the same time. In certain embodiments, the oncolytic virus and the immunomodulatory agent can be administered sequentially in any order (e.g., the oncolytic virus is administered to the subject before the immunomodulatory agent is administered; or the oncolytic virus is administered to the subject after the immunomodulatory agent is administered) or at different points in time (e.g., the oncolytic virus and the immunomodulatory agent are administered to the subject on the same day but different hours; the oncolytic virus and the immunomodulatory agent are administered to the subject in the same week but on different days).

5. Kits

The present invention further provides kits that include an oncolytic virus expressing an IL-36 cytokine or a functional fragment thereof (e.g., oncolytic viruses disclosed in Section 2), or a pharmaceutical composition including said oncolytic virus (e.g., pharmaceutical compositions disclosed in Section 3).

In certain embodiments, a kit of the present disclosure includes an oncolytic virus that comprises a nucleic acid that encodes an IL-36γ cytokine, e.g., a human IL-36 cytokine, or a functional fragment thereof.

In certain embodiments, the kit disclosed herein can further include instructions. In certain embodiments, the instructions include a description of the oncolytic virus, and optionally a description of other components included in the kit. In certain embodiments, the instructions further include a description of methods for administration, including methods for determining the proper state of the subject, the proper dosage amount, and/or the proper administration method for administering the modified virus. In certain embodiments, the instructions further include guidance for monitoring the subject over duration of the treatment time.

In certain embodiments, the kit disclosed herein includes a device for administering the oncolytic virus to a subject.

Any suitable devices known in the art for administering medications and pharmaceutical compositions can be included in the kits disclosed herein. For example, and not by way of limitation, suitable devices include, a hypodermic needle, an intravenous needle, a catheter, a needle-less injection device, an inhaler and a liquid dispenser, such as an eyedropper. In certain embodiments, an oncolytic virus to be delivered systemically, for example, by intravenous injection, can be included in a kit with a hypodermic needle and syringe.

In certain embodiments, the kit disclosed herein can further include an immunomodulatory agent (e.g., immunomodulatory agents disclosed in Section 4.1). In certain embodiments, the immunomodulatory agent is an immune checkpoint inhibitor. In certain embodiments, the immune checkpoint inhibitor is selected from anti-PD1 antibodies, anti-PD-L1 antibodies, anti-CTLA-4 antibodies, anti-BTLA antibodies, anti-TIM3 antibodies, anti-LAG-3 antibodies, and any combinations thereof.

EXAMPLE

The presently disclosed subject matter will be better understood by reference to the following Example, which is provided as exemplary of the presently disclosed subject matter, and not by way of limitation.

Example 1: IL-36γ-Armed Oncolytic Virus Exerts Therapeutic Efficacy Through Induction of Potent Adaptive Antitumor Immunity Tumor microenvironment is highly immunosuppressive and contributes to resistance to immunotherapy (Gajewski et al., *Nat Immunol* 14, 1014-1022 (2013)). Lack of immune-stimulating "alarmin" cytokines in the tumor microenvironment can pose a major obstacle for immune checkpoint inhibitor-based immunotherapy (Nagarsheth et al., *Nat Rev Immunol* 17, 559-572 (2017); Gajewski et al., *Nat Immunol* 14, 1014-1022 (2013); Lu et al., *J Mol Med (Berl)* 94, 535-543 (2016)). Therefore, effective delivery of cytokines to the tumor microenvironment is a promising strategy for improving cancer immunotherapy.

Interleukin-36γ (IL-36γ), formerly IL1F9, is a member of the IL-1 family (Bassoy et al., *Immunol Rev* 281, 169-178 (2018)). IL-36 has been shown to be induced in lining tissue cells such as keratinocytes and bronchial epithelia, and tissue innate immune cells, such as macrophages and dendritic cells. IL-36 is believed to be an "alarmin" in the damaged tissue (Gresnigt et al., *Eur J Immunol* 43, 416-426 (2013); Lian et al., *J Invest Dermatol* 132, 1346-1353 (2012)). IL-36γ binds to IL-36R (IL-1Rrp2) and IL-1RAcP, and is involved in the activation of various immune cells such as dendritic cells (DCs), T-cells, and NK cells (Mutamba et al., *Eur J Immunol* 42, 607-617 (2012); Wang et al., *Cancer Cell* 28, 296-306 (2015); S. Vigne et al., *Blood* 118, 5813-5823 (2011)). It has been shown that IL-36γ can transform tumor microenvironment and promote type 1 lymphocyte-mediated antitumor immunity (Wang et al., *Cancer Cell* 28, 296-306 (2015)). It has also shown that IL-36γ can coordinate with T-bet in therapeutic DC-mediated promotion of ectopic lymphoid organogenesis in tumor microenvironment, which is associated with the antitumor efficacy of DC-mediated cancer vaccine (Weinstein et al., *Oncoimmunology* 6, e1322238 (2017)). The efficacy of IL-36 as a tumor therapeutic agent relies upon the amount of IL-36 that can be delivered into the tumor, which is associated with the antitumor activity and the toxicity of IL-36.

Oncolytic virus (OV)-based therapy is a promising cancer immunotherapy (Bartlett et al., *Mol Cancer* 12, 103 (2013); Lichty et al., *Nat Rev Cancer* 14, 559-567 (2014); Lawler et al., *JAMA Oncol* 3, 841-849 (2017)). Oncolytic viruses can induce oncolysis of infected cancer cells and tumor-associated stromal cells, usually in the form of immunogenic cell death. Immunogenic cell death can further induce adaptive antitumor immune responses (Bartlett et al., *Mol Cancer* 12, 103 (2013)). There have been genetically engineered oncolytic vaccinia viruses (VVs) developed to achieve tumor selectivity (Guo et al., *J Immunother Cancer* 7, 6 (2019)). For example, oncolytic VVs with a single deletion of the viral gene tk (also known as vv.TK-) (McCart et al., *Gene Ther* 7, 1217-1223 (2000)), oncolytic VVs with a double deletion of viral genes tk and vgf (also known as vv.DD) (McCart et al., *Cancer Res* 61, 8751-8757 (2001)), and oncolytic VVs with a triple deletion of viral genes tk, spi-1 and spi-2 (also known as vv.TD) (Yang et al., *Gene Ther* 14, 638-647 (2007)). Certain studies have shown that oncolytic VVs with these three genetic backbones can have relatively high tumor selectivity. Phase I clinical trials have shown the safety of vv.DD but minimum efficacy in most human patients with advanced solid cancer other than melanoma (Zeh et al., *Mol Ther* 23, 202-214 (2015); Downs-Canner et al., *Mol Ther* 24, 1492-1501 (2016)). In contrast, Pexa-Vec has shown better efficacy in phase II trial (Heo et al., *Nat Med* 19, 329-336 (2013)), and it is being tested in a global PHOCUS phase III trial in combination with sorafenib (Nexavar) for hepatocellular carcinoma. Despite the progress in clinical trials, new approaches to improve OV-based cancer therapy is needed.

Certain studies have shown that OV-elicited antitumor adaptive immune responses are essential in OV-mediated therapeutic efficacy (Bartlett et al., *Mol Cancer* 12, 103 (2013); Lichty et al., *Nat Rev Cancer* 14, 559-567 (2014); Lawler et al., *JAMA Oncol* 3, 841-849 (2017); Guo et al., *J Immunother Cancer* 7, 6 (2019); Kaufman et al., *Nat Rev Drug Discov* 14, 642-662 (2015)). Some strategies have been designed and tested to further improve the antitumor immunity of OVs. For example, OVs were engineered to express heat-shock proteins, cytokines, or costimulatory molecule to enhance tumor immunogenicity (Zafar et al., *Oncoimmunology* 6, e1265717 (2017); Zamarin et al., *Nat Commun* 8, 14340 (2017); Liu et al., *Nat Commun* 9, 4682 (2018)); OVs were used with other immunotherapy regimens (Zamarin et al., *Sci Transl Med* 6, 226ra232 (2014); Liu et al., *Nat Commun* 8, 14754 (2017); Samson et al., *Sci Transl Med* 10, eaam7577 (2018)). Talimogene laherparepvec (T-VEC) is an FDA approved OV that is a genetically engineered GM-CSF expressing oncolytic herpes simplex virus (Andtbacka et al., *J Clin Oncol* 33, 2780-2788 (2015)). Clinical benefit of T-VEC, however, is limited in advanced melanoma patients (Andtbacka et al., *J Clin Oncol* 33, 2780-2788 (2015)). Therefore, synergistically combining the antitumor activities of oncolytic VVs and cytokines remains a difficult task.

The present disclosure provides oncolytic vaccinia viruses expressing a secreted form of interleukin-36γ (IL-36γ-OVs). The present disclosure further provides that IL-36γ-OVs had increased therapeutic efficacies in murine models of colorectal, melanoma, and pancreatic cancers, leading to extended survival of these murine models, as compared to OVs that did not express IL-36γ. IL-36γ-OVs-elicited adaptive immunity can be dependent on the presence and levels of CD4$^+$ and CD8$^+$ T cells. In addition, IL-36γ-OVs modulated the tumor microenvironment by inducing the infiltration of lymphocytes and DCs, but not MDSCs and M2 type tumor-associated macrophages (TAMs). Moreover, IL-36γ-OV increased the number of both tumor antigen- and viral antigen-specific CD4$^+$ and CD8$^+$ T cells, as compared to OVs that did not express IL-36γ. The presently disclosed data demonstrates that IL-36γ can increase OV-elicited antitumor activities by enhancing adaptive T cell-mediated immune responses, and by promoting immunogenic tumor microenvironment.

The present disclosure provides oncolytic VVs expressing an active form of IL-36γ. The present disclosure leverages direct oncolytic and tumor selectivity of oncolytic VVs and immune stimulatory effect of IL-36γ for the induction of antitumor activity. The present disclosure tested the antitumor efficacy of IL-36γ-armed VV in several murine syngeneic tumor models. The underlying immune mechanisms were investigated subsequently. The present disclosure established the feasibility of tumor-specific delivery of IL-36γ by oncolytic VV and elucidate the mechanisms of antitumor synergism between these two tumor immune therapeutics.

Construction and In Vitro Characterization of Oncolytic Poxviruses Expressing IL-36γ.

Three IL-36γ-armed VVs, including vvTK-IL36γ, vvDD-IL36γ, and vvTD-IL36γ, were constructed by inserting an active form of IL-36γ into three VV backbones with different tumor selectivity and oncolytic activities (FIG. 1A). The expression of IL-36γ from the virus-infected HeLa cells was verified. At 48-hour post-infection with the control VV (vvTK-) and vvTK-IL36γ, the level of the secreted IL-36γ in the culture medium was measured by Western blot (FIG. 1B). IL36γ protein was detected in the media from vvTK-IL36γ-infected HeLa cells, but not from mock-infected, or control virus-infected HeLa cells. B16-IL-36γ melanoma cells, in which IL-36γ-expressing plasmids were stably transfected (Wang et al., *Cancer Cell* 28, 296-306 (2015)), served as positive controls. These results demonstrated that the vvTK-IL36γ virus-infected cancer cells synthesized and secreted IL-36γ.

Figure 1D:
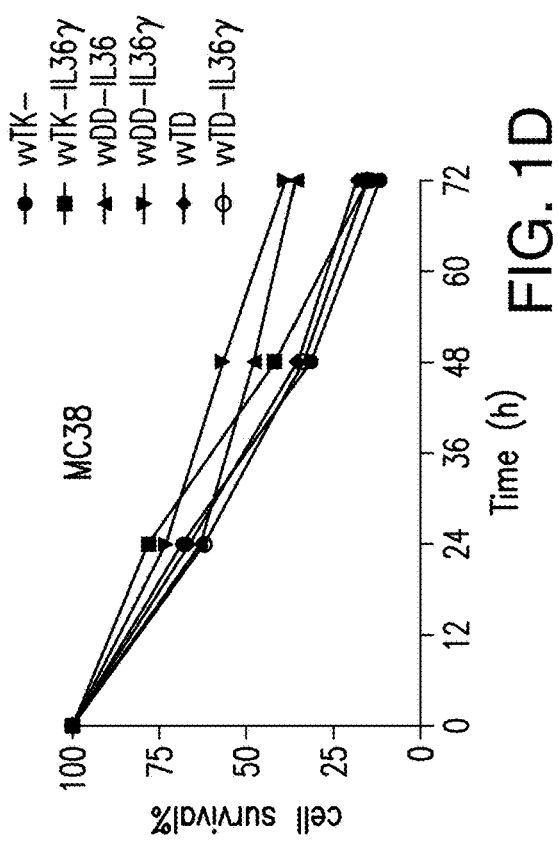
Figure 1F:
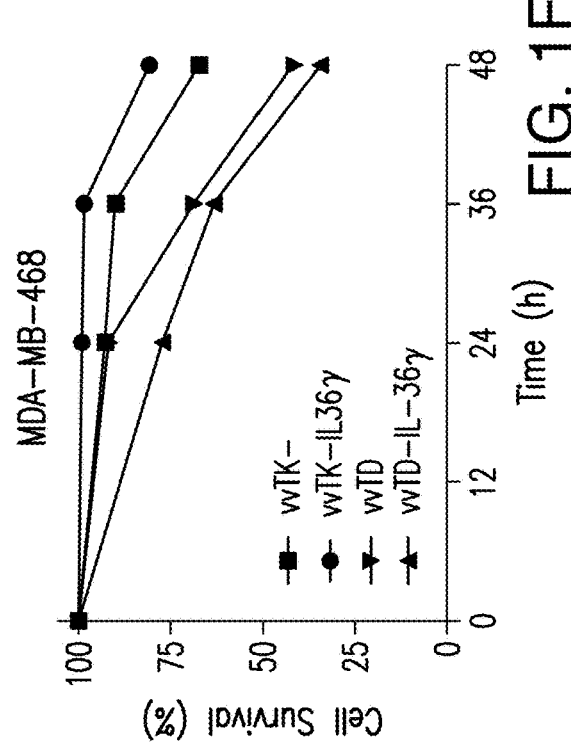
Figure 1C:
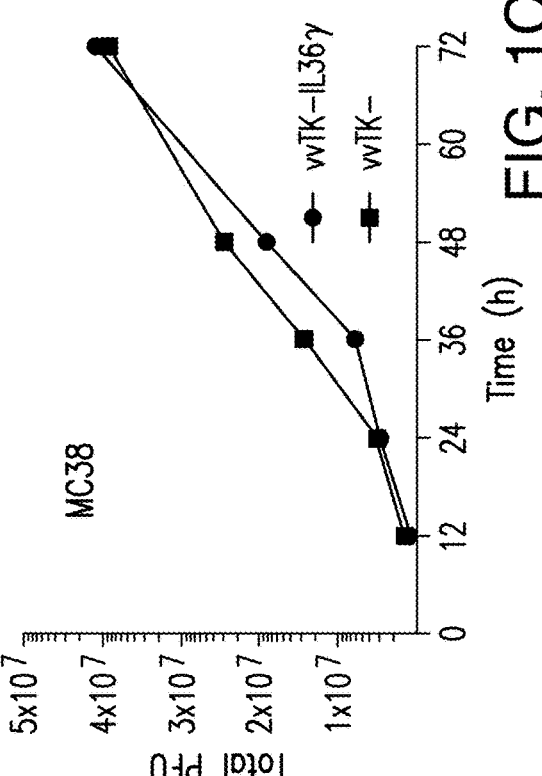
Figure 1E:
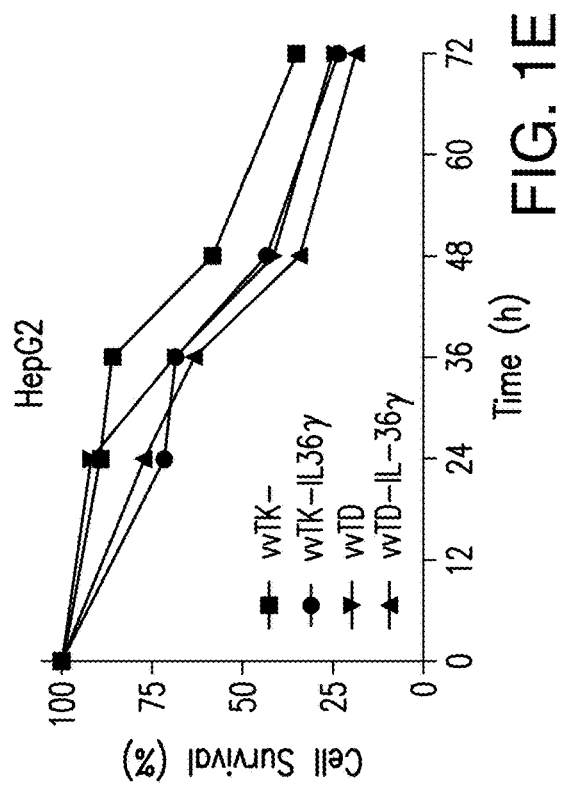

Replication efficiency and oncolytic activities of IL-36γ-expressing OVs were compared with the parental OVs. vvTK-IL36γ and its parental virus vvTK replicated at similar rates in MC38 colon cancer cells which were infected with these OVs (FIG. 1C). Similar oncolytic activities among the three pairs of OVs in MC38 cancer cells were observed (FIG. 1D). Oncolytic potency of the OVs were examined in human liver cancer (HepG2) and breast cancer (MDA-MB-468) cell lines. Again, similar cytolytic kinetics was observed in control oncolytic VVs and IL-36γ-armed VVs (FIGS. 1E & 1F). Together, these data demonstrated that genetic addition of the IL-36γ gene cassette to the VV genome did not affect infectivity and oncolytic activities of viruses. No major differences were observed between three versions of IL36γ-expressing OVs.

IL36γ-Armed OV Induced a Stronger Antitumor Activity in MC38 Colon Cancer Model.

Figure 2A:
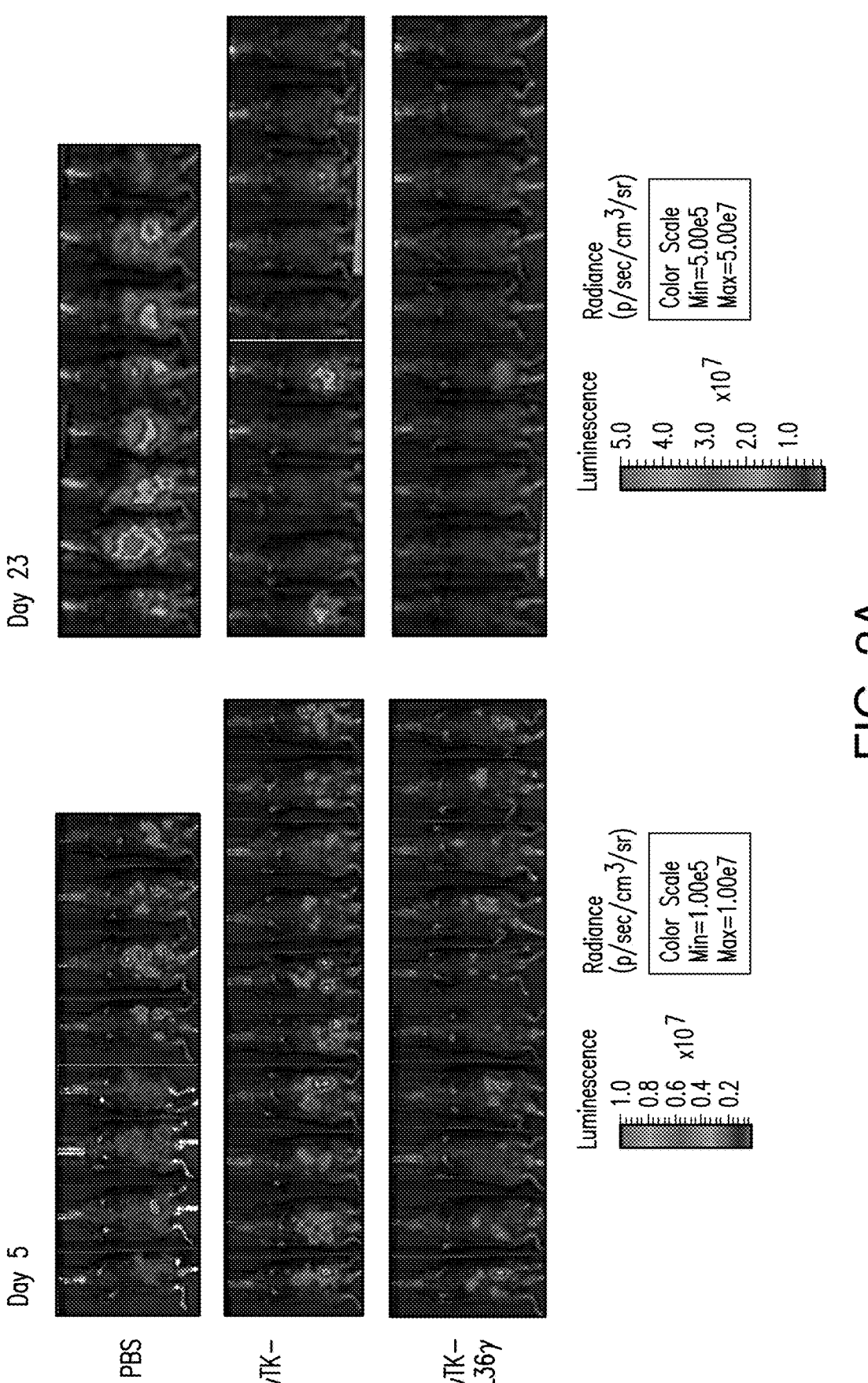
FIGS. 2A-2C provide that IL-36γ-armed OV led to complete regression of peritoneal MC38-luc carcinomatosis, and resistance of tumor cell re-challenge by parental MC38-luc colon cancer and partially by Lewis lung carcinoma. B6 mice were inoculated i.p. with 5.0×10⁵ MC38-luc cells. On day 5, mice were bioluminescence imaged to exclude mice with no tumor. Remaining mice were randomly divided into 3 groups, and were treated with PBS, vvTK-, and vvTK-IL-36γ at a dose of 1.0×10⁸ pfu/mouse.
Figures 2B, 2C:
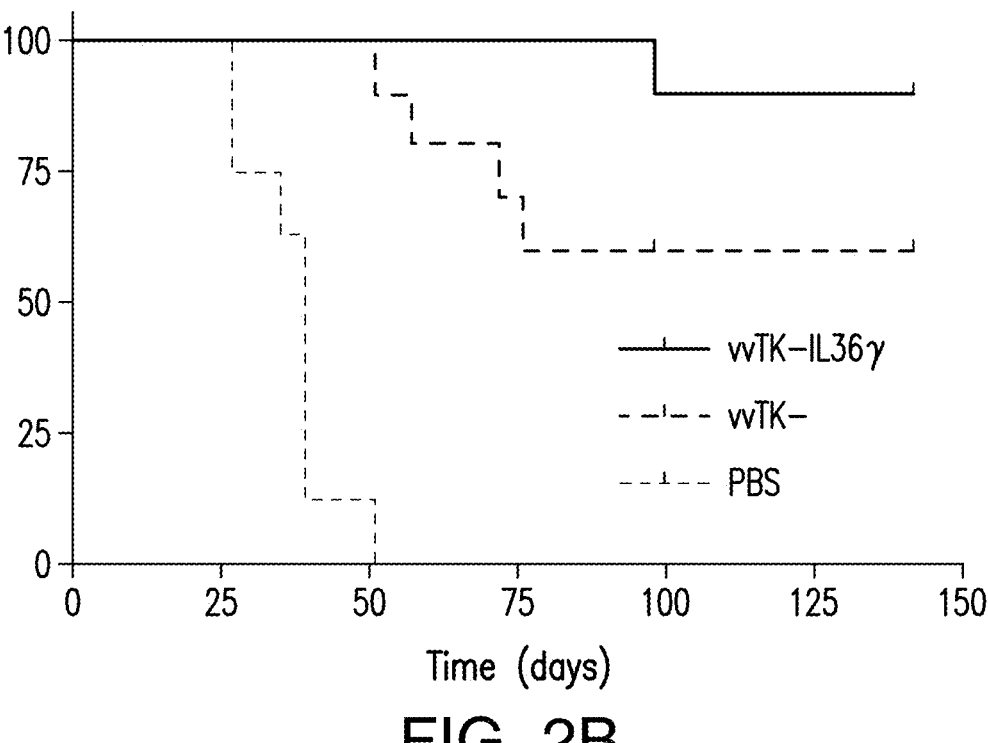

Antitumor activities of the presently disclosed OVs were examined in an intraperitoneal MC38 tumor model as described previously (Guo et al., *Gene Ther* 17, 1465-1475 (2010)). On day 5, mice were imaged for tumor burden and tumor-free mice were excluded. Remaining mice were randomly assigned to groups (FIG. 2A). PBS, vvTK, or vvTK-IL36γ were administered to mice intraperitoneally (i.p.) at 1.0×10$^8$ pfu per mouse. Mice were monitored for toxicity and efficacy as indicated by appearance, tumor size, and survival. Parental virus vvTK treatment prolonged the survival of tumor-bearing mice (FIG. 2B) as compared to the control vvTK, whereas vvTK-IL36γ treatment further prolonged the survival of tumor-bearing mice (FIG. 2B). At the end of the experiment (total 142 days), 6 out of 10 mice treated with vvTK were tumor-free, and 9 out of 10 mice treated vvTK-IL36γ were tumor-free (p=0.029). To determine whether antitumor memory T cells were generated in the tumor-free mice, the tumor-free mice were re-challenged with MC38 tumor cells (FIG. 2C). None of the tumor-free mice grew any MC38 tumor after the re-challenge. Seven out of 9 mice cured by vvTK-IL36γ were protected from the challenge with an unrelated Lewis lung cancer, whereas 2 out of 6 mice cured by vvTK were protected from the challenged with the unrelated Lewis lung cancer (p=0.09; t-test). These results suggested that the adaptive antitumor immunity against MC38 tumor might have cross-reacted with Lewis lung cancer. In the control group, MC38 and Lewis lung cancer grew in 100% naïve mice. These results indicated that IL-36γ-armed OVs were strong antitumor agents that can induce memory antitumor immune responses.

Figures 8A, 8B, 8C, 8D:
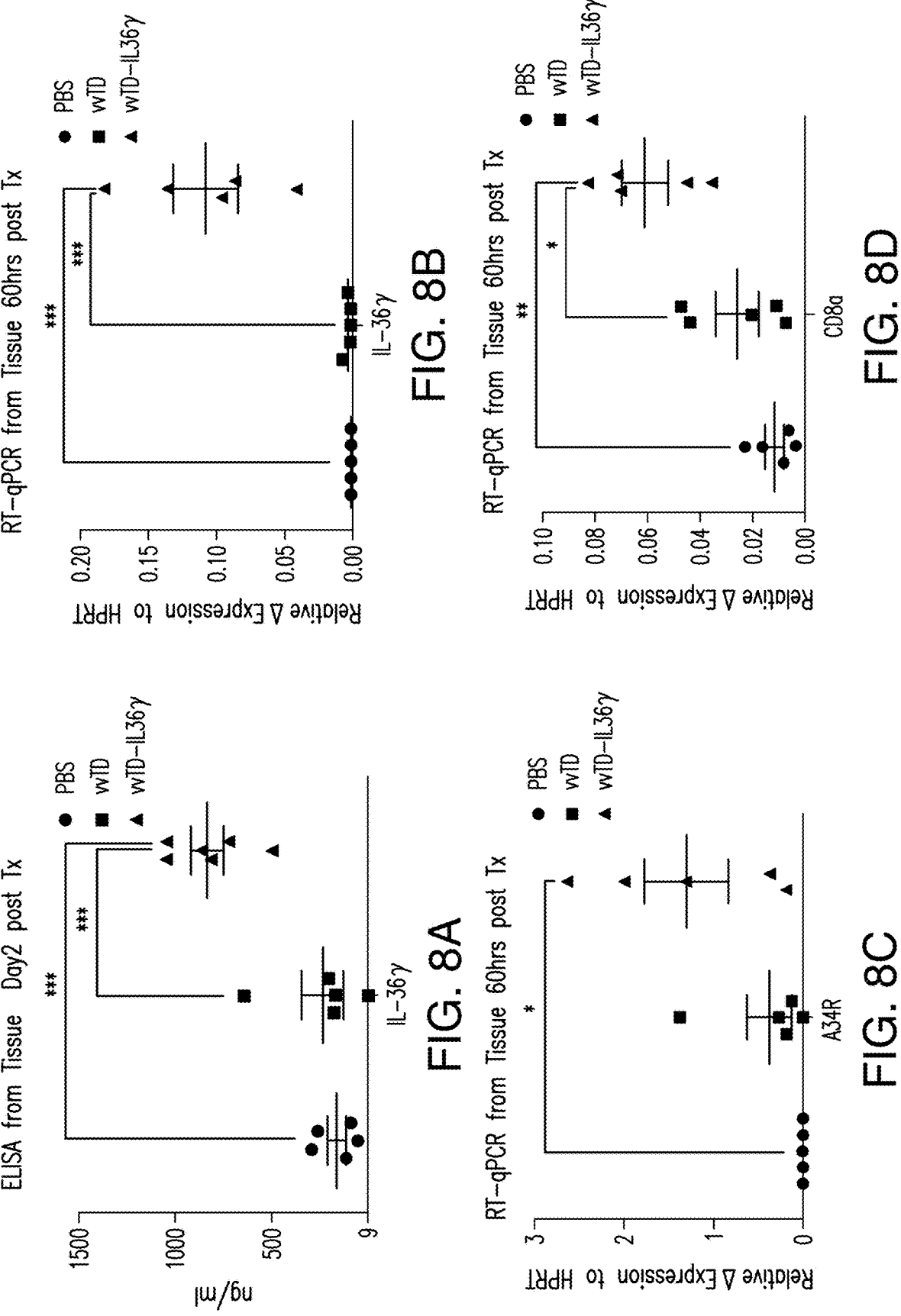
FIGS. 8A-8G provide that vvTD-IL36γ increased IL-36γ production in MC38 peritoneal carcinomatosis tissue. Two days after oncolytic virotherapy, RNA and intra- and extracellular fluid were extracted from peritoneal carcinomatosis homogenates. Each data point represented one mouse. ELISA analysis revealed that IL-36γ was significantly increased in intra- and extracellular fluid of tumor homogenates from cytokine-expressing virus in comparison to parental virus and PBS control on day 2 (FIG. 8A). The IL-36γ level was maintained elevated on day 6 following immunotherapy in the cytokine-expressing virus treatment group (FIG. 8E). Consistent with quantitative protein findings, RT-qPCR showed increased IL-36γ relative expression in total RNA of tumor homogenates 60 hours following virotherapy (FIG. 8B), but not on day 6 (FIG. 8F). This could be due to a decrease in expression that was not yet reflected in protein levels explained by the longer half-life. The expression of vaccinia virus-specific gene A34R was elevated two days following immunotherapy in cytokine-expressing virus treated animals (FIG. 8C) but normalized to untreated control animals on day 6 post therapy (FIG. 8G). Relative CD8a expression 60 hours past immunotherapy in tumor tissue was higher in the vvTD-IL36γ-YFP treated animals than in both other treatment groups (FIG. 8D). $*p<0.05$. $p<0.01$. $*p<0.001$.
Figure 8F:
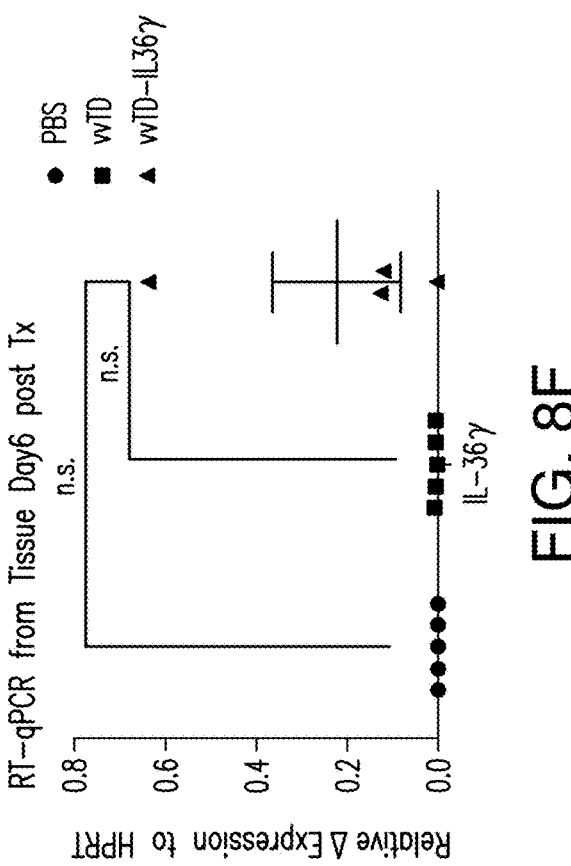
Figure 8E:
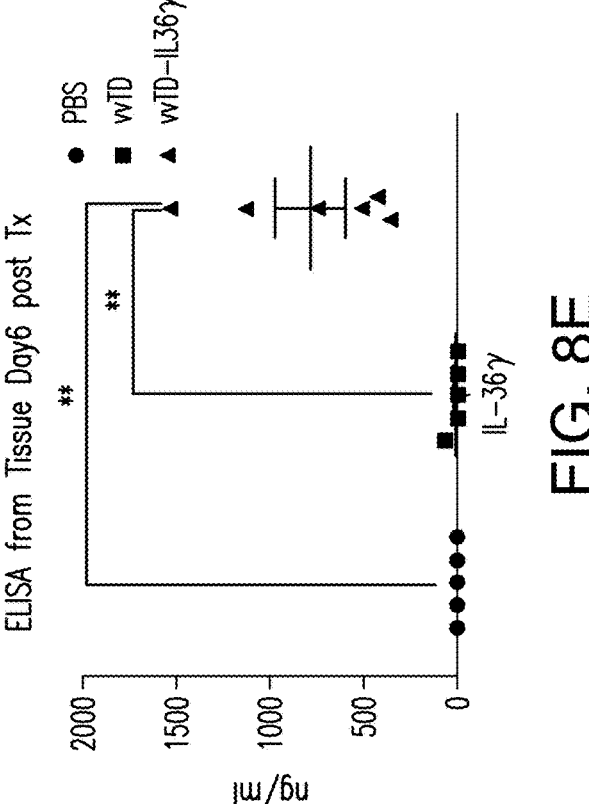
Figure 8G:
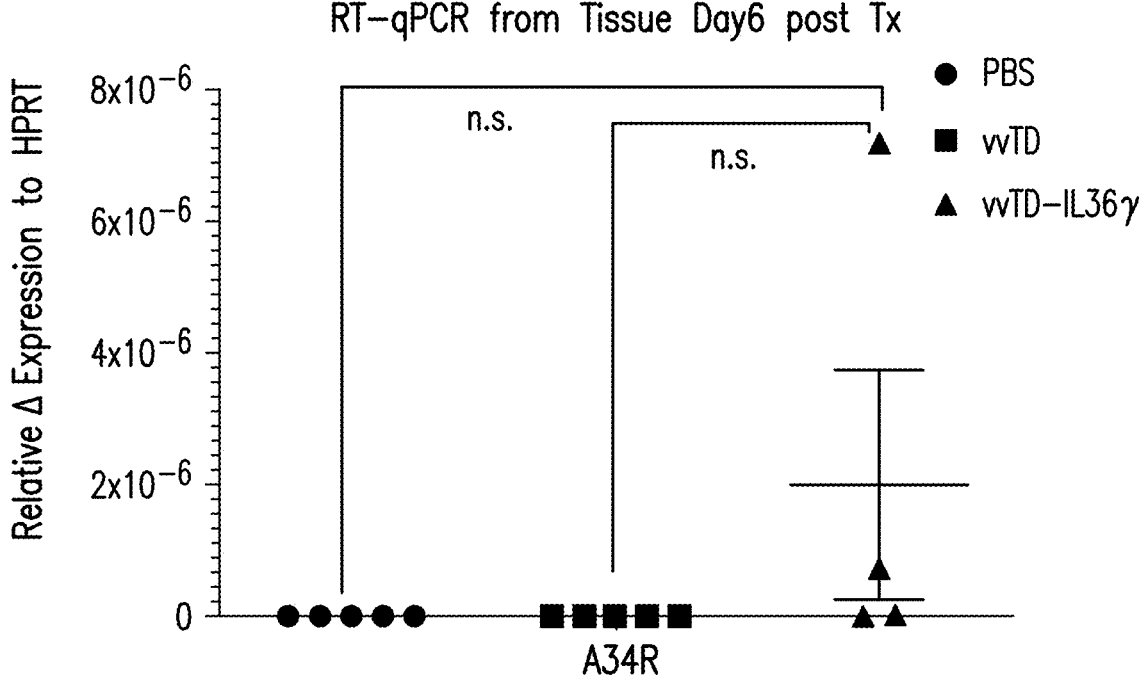

The kinetics of viral replication and IL-36γ expression in tumor tissues were examined (FIGS. 8A-8G). IL-36γ levels were significantly increased in tumor homogenates on day 2 and day 6 after administration of OVs as measured by ELISA (FIGS. 8A and 8E). The elevated levels of IL-36γ were also confirmed at the mRNA level by RT-qPCR (FIGS. 8B and 8F). As for mRNA of viral marker gene A34R, it was detected on day 2, but reduced to basal levels on day 6 (FIGS. 8C and 8G). Relative CD8a expression 60 hours past immunotherapy in tumor tissue was higher in the vvTD-IL36γ-YFP treated animals than in both other treatment groups (FIG. 8D). These data demonstrated that the viruses were replicated for a few days, and by day 6, they were reduced to low levels. In contrast, IL-36γ protein was sustained at a high level in the infected tumor tissues 6 days after OV administration.

The IL-36γ-Armed OVs were More Efficacious in Two Other Syngeneic Tumor Models.

Figures 3A, 3B:
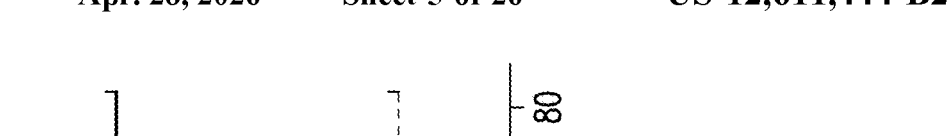
FIGS. 3A-3B provide that vvTK-IL36γ exerted potent antitumor activity, and prolonged the survival of mice bearing tumors of melanoma (B16) and pancreatic cancer (panc02-luc).
Figure 13A:
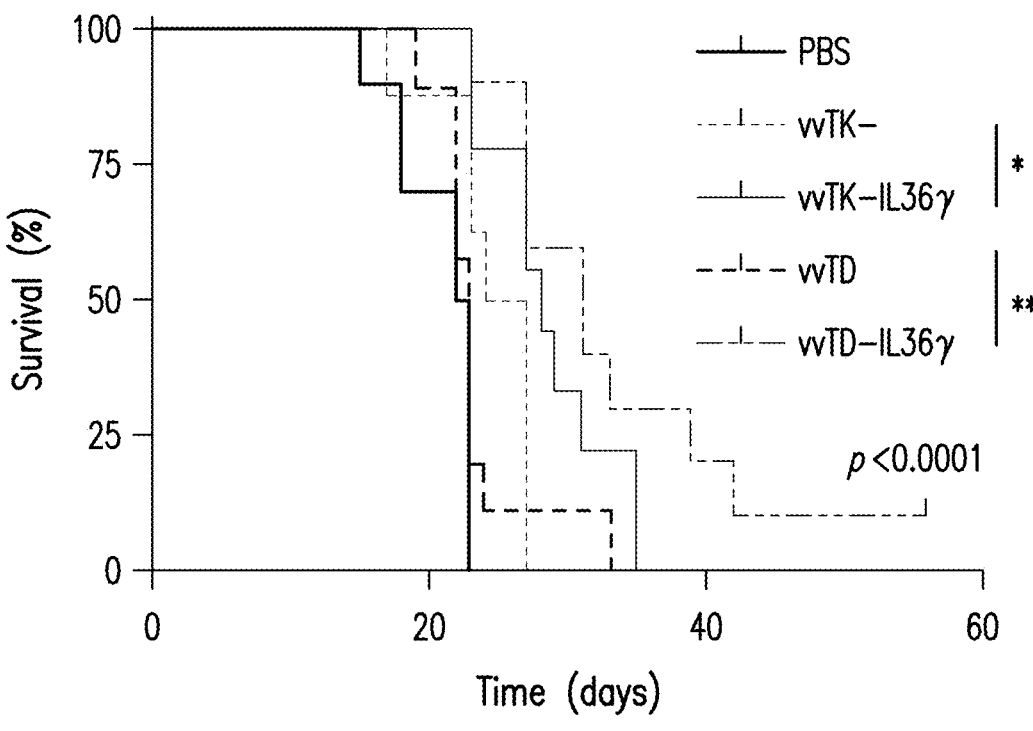
FIG. 13A-13D provide that vvTK-IL36γ exerted potent antitumor activity and prolonged the survival of mice bearing tumors of melanoma (B16), pancreatic cancer (panc02-luc) and MC38 colon cancer.
Figure 13B:
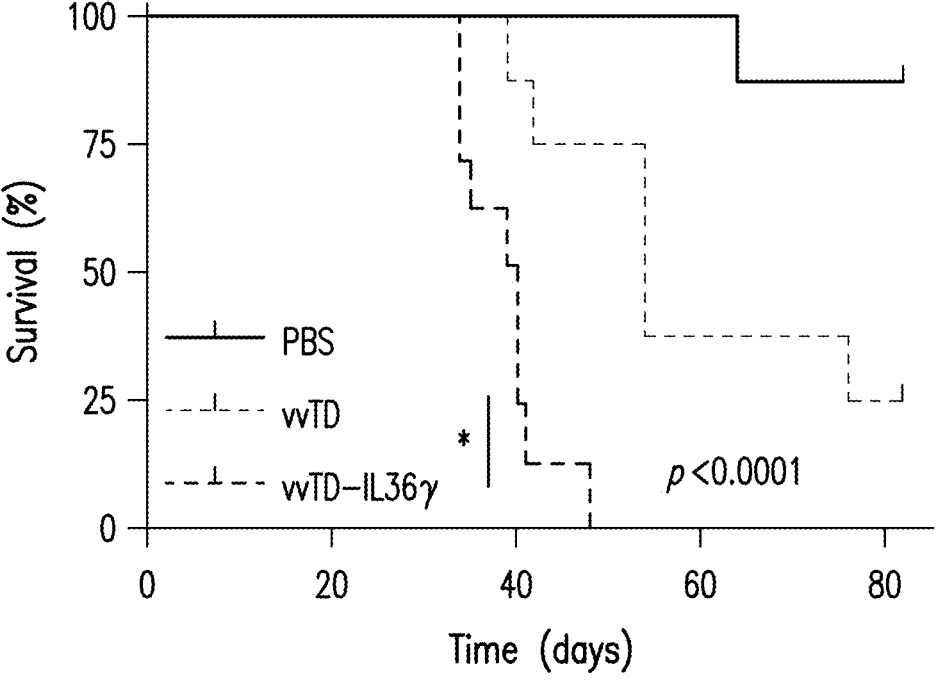
Figures 13C, 13D:
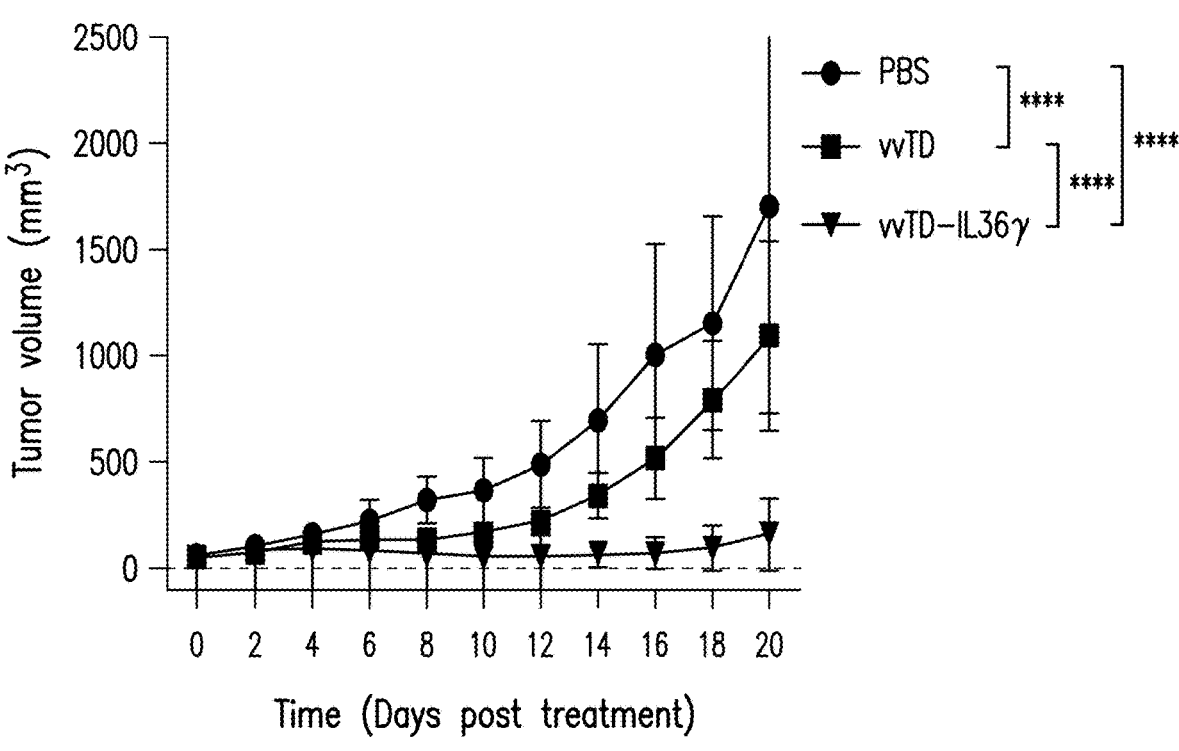

B16, panc02 and MC38 syngeneic tumor models were established. The tumor-bearing mice were treated with OVs. In the B16 tumor model (FIGS. 3A and 13A), vvTK-IL36γ and vvTD-IL36γ were more effective in prolonging survival than their corresponding parental viruses (vvTK (p=0.0236) and vvTD (p=0.0016)). In the panc02 tumor model (FIGS. 3B and 13B), vvTD-IL36γ was more effective in prolonging survival than vvTD (p=0.017). In MC38 colon cancer model (FIGS. 13C and 13D) vvTD-IL36γ was more effective in prolonging survival than vvTD. These data demonstrated that IL-36γ-armed OVs were potent antitumor agents in multiple syngeneic murine tumor models.

IL-36γ-Expressing OV Induced Greater Immune Cell Infiltration into the Tumor.

Figure 4A:
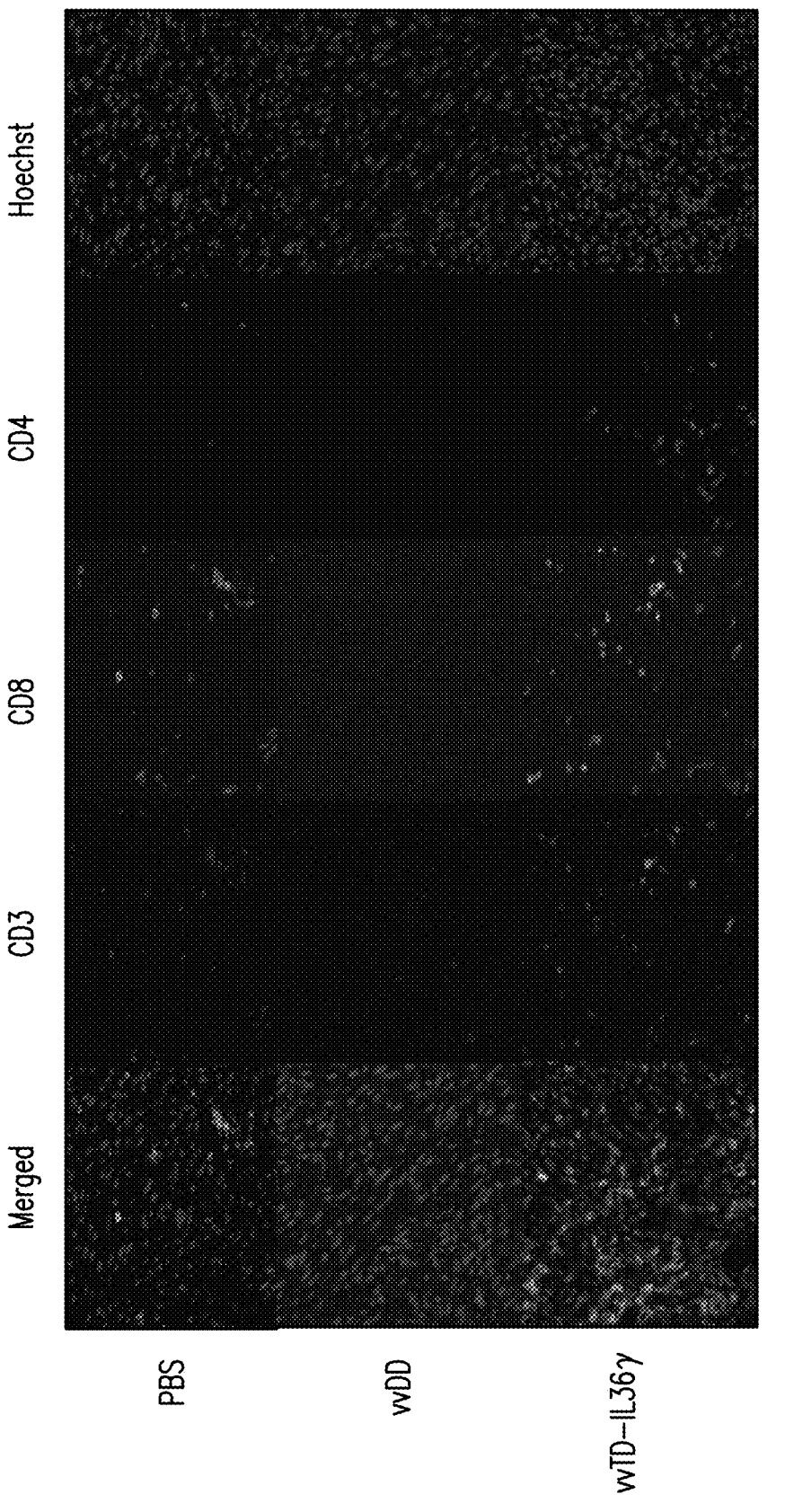
FIGS. 4A-4B provide that treatment with IL-36γ-armed OV increases the number of T cells in MC38 solid colon tumor tissue. B6 mice were s.c. inoculated with 5.0×10⁵ MC38 cancer cells. When the tumor size reached ~5×5 mm in diameter, PBS, vvDD, vvDD-IL36γ (1.0e8 pfu per tumor) was injected intratumorally (n=6~8/group).
Figure 4B:
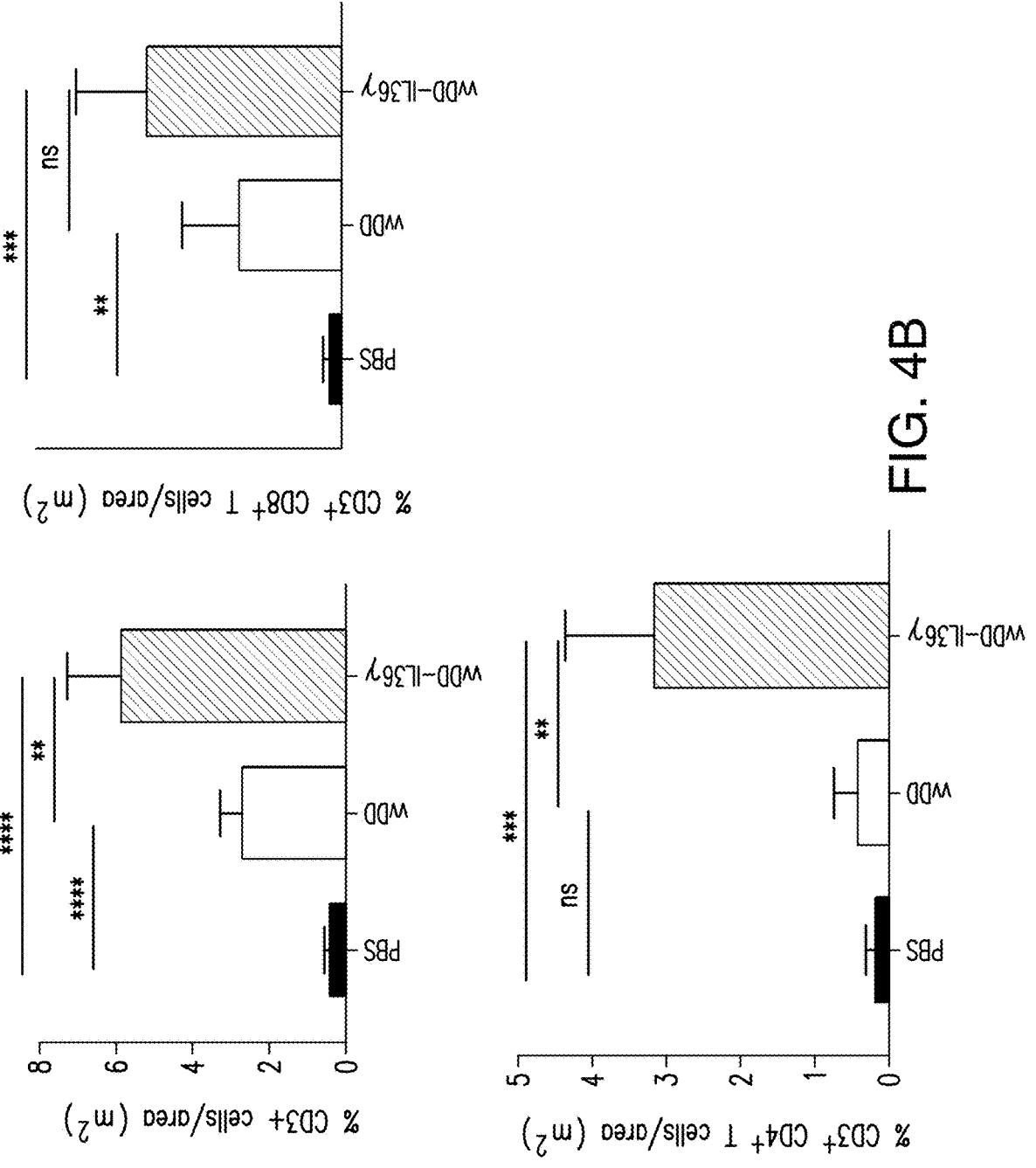

Cellular mechanisms underlying stronger antitumor activities of IL-36γ-OV were studied using MC38 subcutaneous tumor model. When tumors reached a diameter of about 5.0 mm, PBS, vvDD or vvDD-IL-36γ were injected intra-tumorally at 1.0×10⁸ pfu per mouse. On day 4 post treatment, tumor tissue sections were analyzed by immuno-fluorescence staining. Immune cell markers such as CD3, CD4 and CD8 were analyzed to assess the levels of infiltrating T cells in the tumor tissues (FIGS. 4A and 4B). vvDD increased the density of CD3⁺ cells in the tumors as compared to PBS. vvDD-IL-36γ further increased the density of CD3⁺ cells in the tumors as compared to vvDD. Additional analyses indicated that vvDD increased CD8⁺ T cells in the tumors as well. Furthermore, vvDD-IL-36γ showed a trend of a further increase of CD8⁺ T cells as compared to vvDD (FIGS. 4A and 4B). In addition, vvDD-IL-36γ treatment resulted in more CD4⁺ T cell infiltration as compared to PBS or vvDD treatment (FIGS. 4A and 4B). In summary, the IL-36γ-OV treatment induced higher levels of T cell infiltration in the tumors.

IL-36γ-Armed OV-Mediated Therapy is Dependent on CD4⁺ and CD8⁺ T Lymphocytes.

Figure 5A:
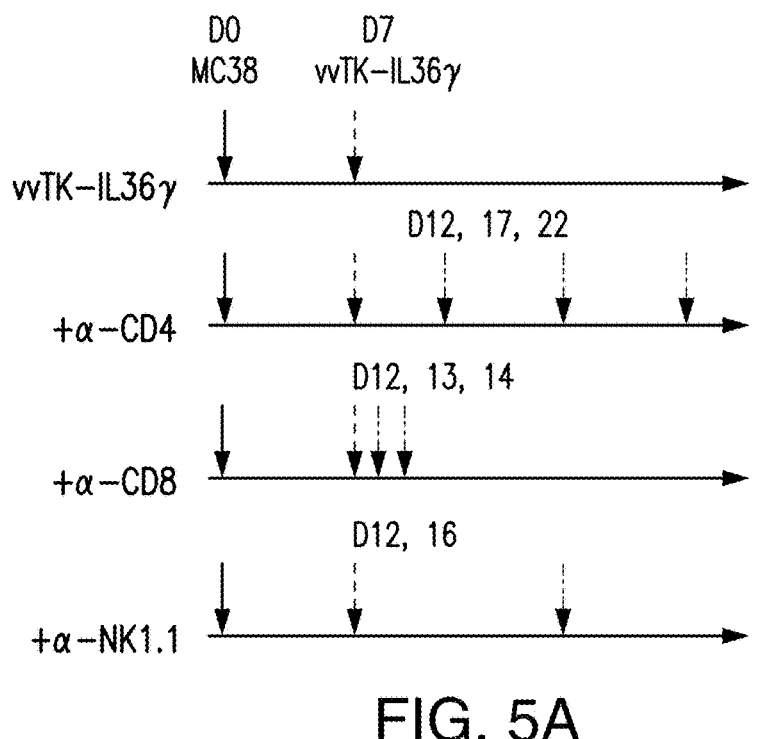
FIGS. 5A-5B provide therapeutic efficacy of IL-36γ-armed OV depends on multiple types of activated immune cells. Peritoneal MC38 tumor-bearing mice were imaged, randomized and injected i.p. with PBS, or 1.0e8 pfu of vvTK-IL36γ.
Figure 5B:
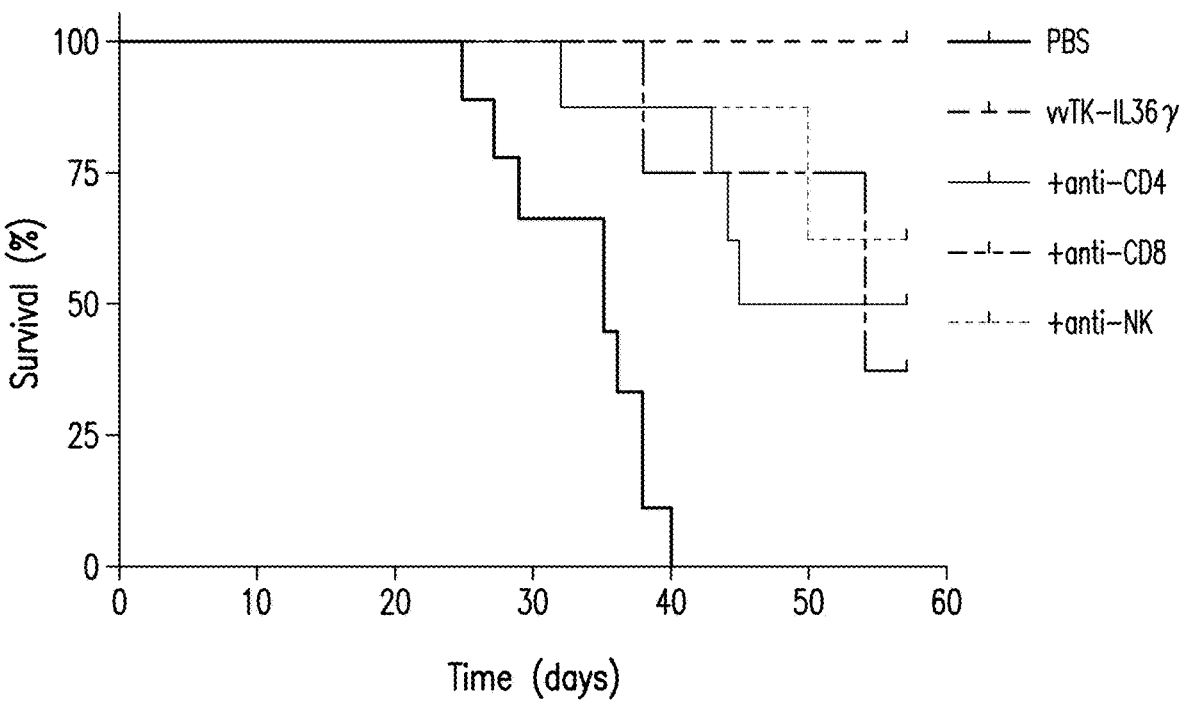

Since T cells were increased by VV-IL36γ, it was then investigated which types of lymphocytes were required for the therapeutic efficacy using the MC38 tumor model. On day 7 after tumor cell inoculation, MC38-tumor-bearing mice were imaged and randomly divided into 5 groups, with one group treated with PBS only and the other four groups treated with vvTK-IL36γ (FIGS. 5A and 5B). The groups of vvTK-IL36γ-treated mice were further treated with PBS, anti-CD4, anti-CD8, or anti-NK1.1 antibodies, respectively, on a schedule as indicated (FIG. 5A). The tumor growth and survival of the mice were monitored (FIG. 5B). Depletion of either CD4⁺ or CD8⁺ T cells significantly reduced the efficacy of vvTK-IL-36γ-mediated virotherapy (p<0.01). It was also found a trend that the therapeutic effect was dependent on NK cells under these conditions (p=0.06).

IL-36γ-Armed OV Enhanced Type 1 Immune Responses in the TME.

Figures 9C, 9D:
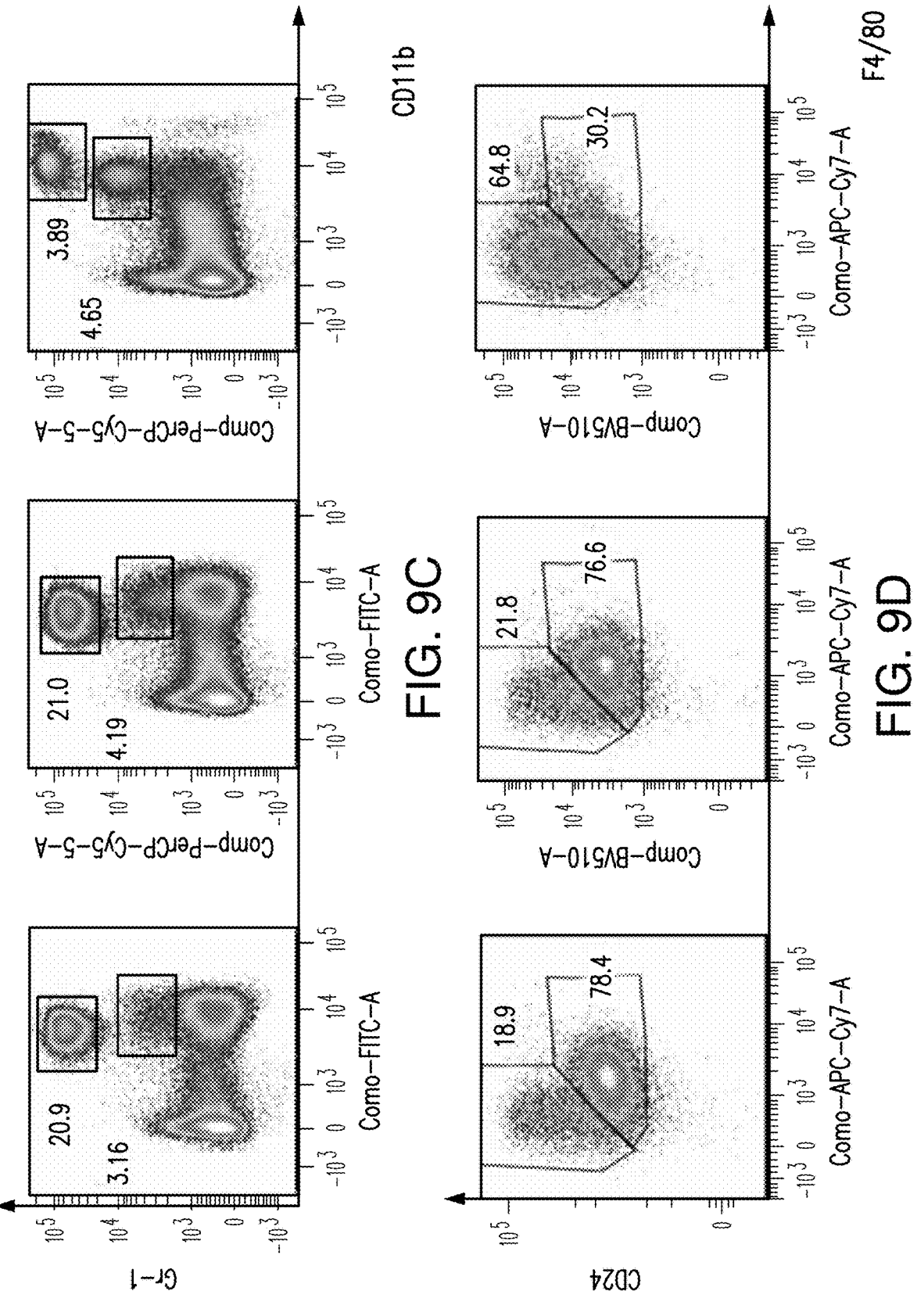
Figures 9E, 9F:
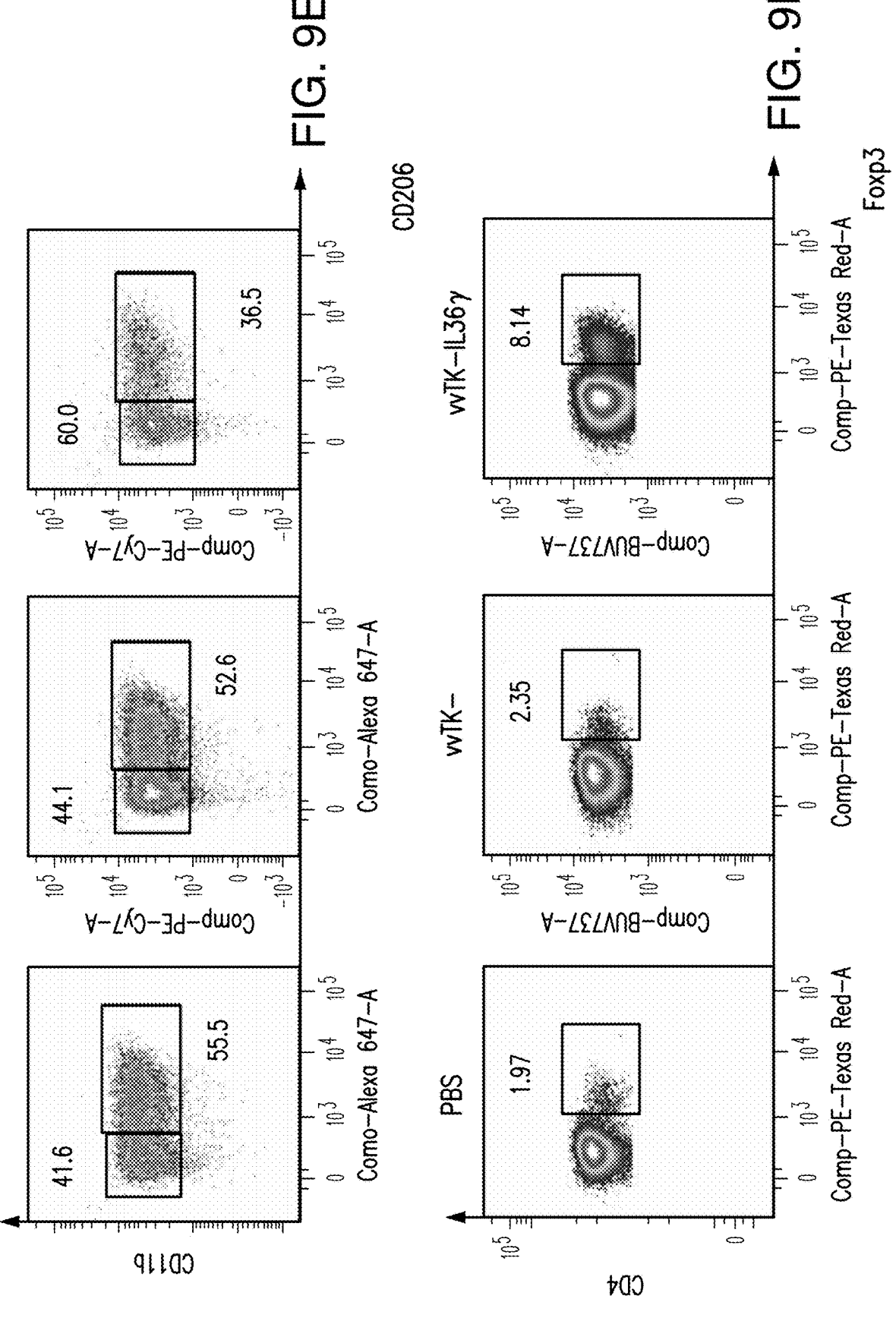
Figure 9F:
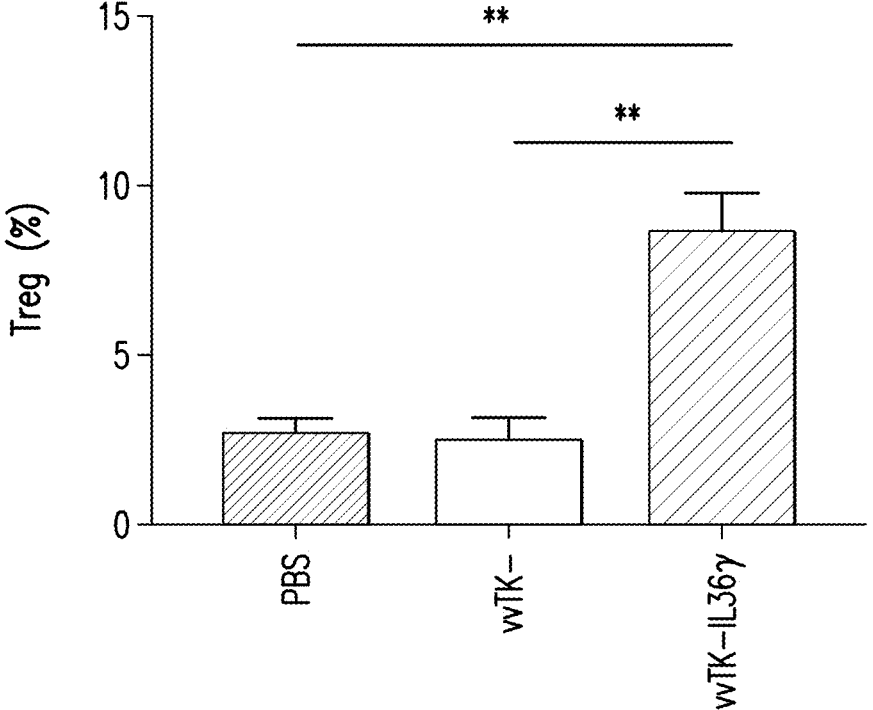
Figure 10F:
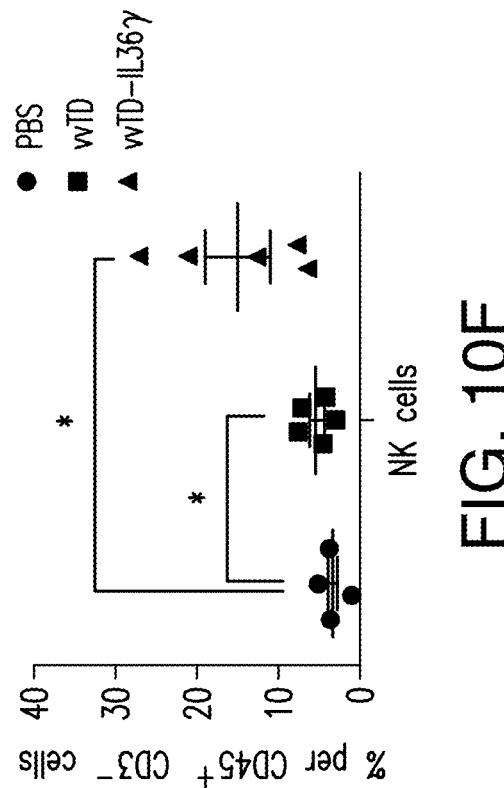
Figure 10E:
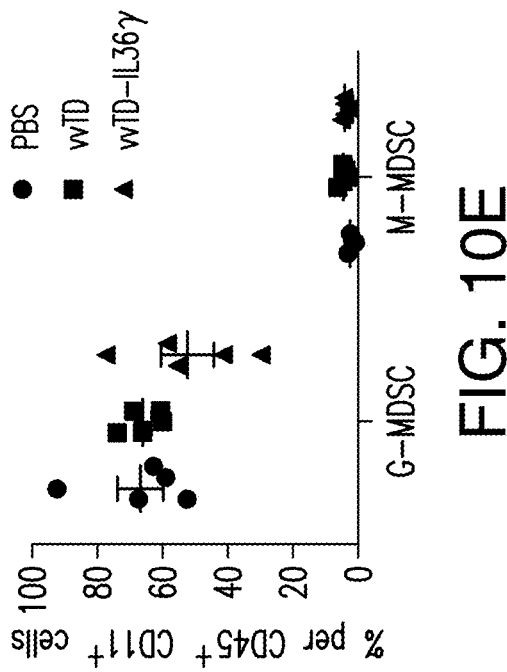
Figure 12B:
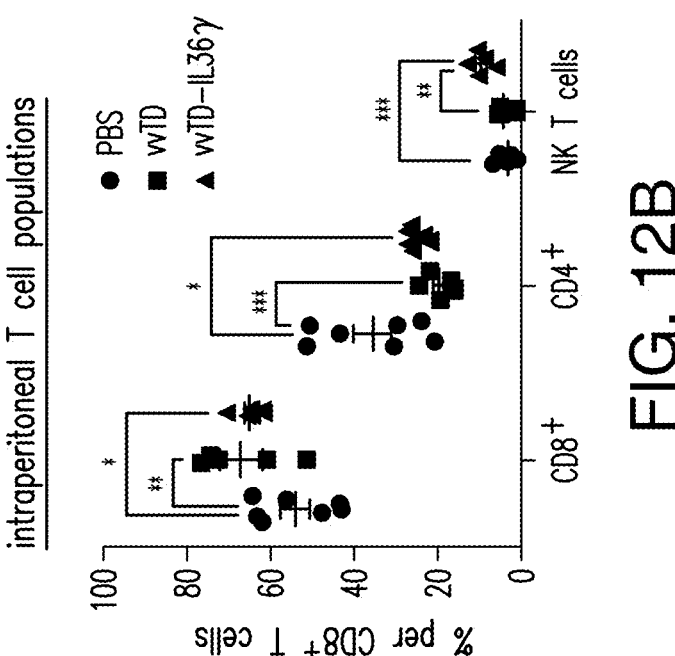
FIGS. 12A-12E provide analysis of lymphocyte subpopulations in lavage specimen 11 days post OV TX.
Figure 12A:
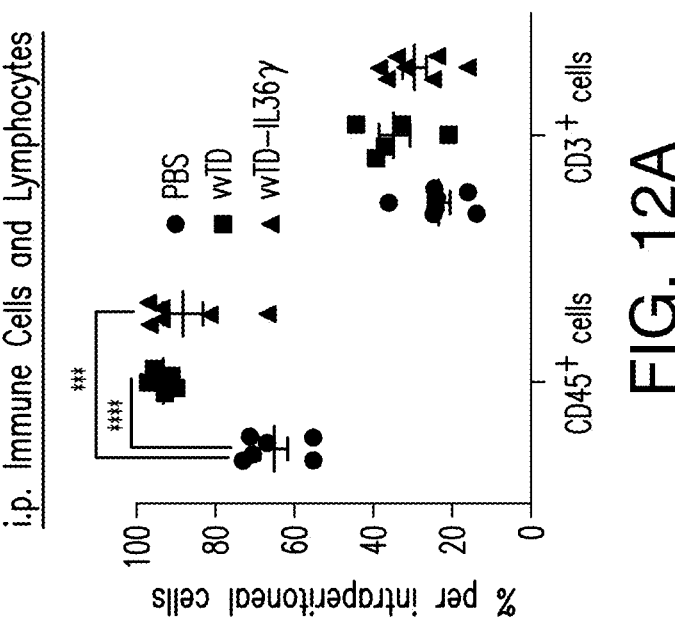
Figures 12C, 12D, 12E:
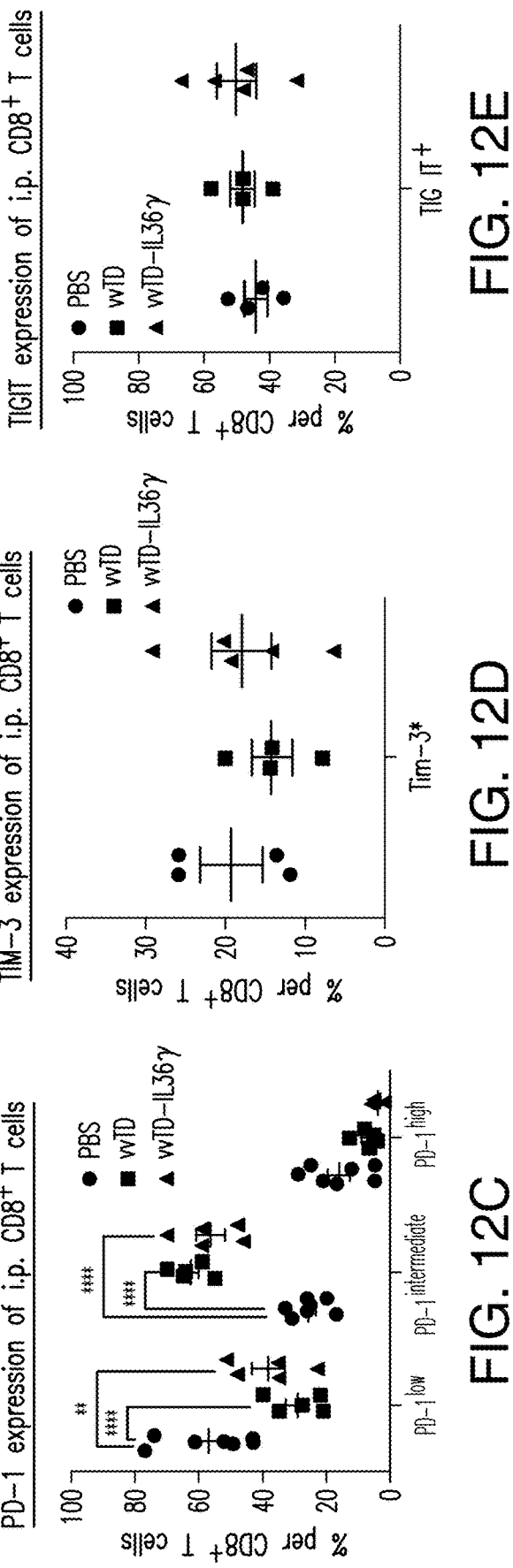

Immune cell components in the tumor microenvironment after VV-IL36γ-treatment were studied. FIGS. 10A-10F provide analysis of immune cells in lavage specimen on day 6 and day 11 post immunotherapy. FIGS. 12A-12E provide analysis of lymphocyte subpopulations in lavage specimen 11 days post OV TX. Cells collected from the peritoneal cavity lavage of tumor-bearing mice on day 6 post viral therapy. Immune cells were analyzed by multi-color flow cytometry (FIGS. 6A-6I and 9A-9F). IL-36γ-OV induced an increase (in percentage) in total lymphocytes (FIGS. 6A and 9A), and especially the cytotoxic CD8+ T cells and NK cells (FIG. 12B). In addition, the frequency of IFN-γ⁺CD8⁺ T cells was greatly increased (FIGS. 6B and 9B). For the myeloid compartment, the frequency of granulocytic myeloid derived suppressor cells (G-MDSC), but not the monocytic MDSC (M-MDSC), was reduced by vvTK-IL36γ treatment as compared to control OV and non-treatment on day 6 after the treatment (FIGS. 6C, 9C, and 10B). In contrast, the percentages of total macrophages and M2-like macrophages (CD206⁺ TAM) were significantly reduced by IL-36γ-OV treatment (FIGS. 6D, 6E, 9D, 9E, and 10A). In addition, the percentage of DC was highly increased by IL-36γ-OV (FIGS. 6F and 9D). However, IL-36γ-OV treatment increased the frequency of Treg (FIG. 9E), which may serve as a self-limiting mechanism for oncolytic VVs. Activation status of CD8⁺ T cells in fractioned CD8⁺ T cell populations were also examined. In the mice treated with vvTD and vvTD-IL36γ, the percentage of naïve CD8⁺ T cells were reduced to less than 5% as compared to ~55% in the non-treatment PBS mice (FIG. 6G). This happened concurrently with the increase of 4-1BB⁺ CD8⁺ T cells, from ~4% in PBS group, up to ~14% in vvTD-treated mice, and further up to 37% in mice treated with vvTD-IL36γ (FIG. 6H). This pattern of changes also happened for the effector memory CD8⁺ T cells (FIG. 6I, p<0.01 between vvTD vs. vvTD-IL36γ). These results indicated that OVs promoted differentiation of naïve CD8⁺ T cells to activated T cells (4-1BB⁺ CD8⁺) and effector memory T cells at the abdominal site, and the expression of IL-36γ further enhanced this effect. Interestingly, among CD8⁺ T cells, the viruses (vvTD and vvTD-IL36γ) induced a shift from low to intermediate levels of PD-1 expression in the peritoneal CD8⁺ T cells (FIG. 12C), which can be good targets for immune checkpoint blockade by anti-PD-1 or anti-PD-L1 antibodies. The expression of other suppressive checkpoint molecules TIM-3 and TIGIT in CD8$^+$ T cells were not changed by the OVs (FIG. 12D, 12E). Together, these data indicated that IL-36γ shaped a more immunogenic tumor microenvironment and enhanced the adaptive antitumor immunity.

IL-36γ-Armed OV Promoted Tumor Antigen-Specific CD8$^+$ T Cells.

Figures 7A, 7B, 7C, 7D:
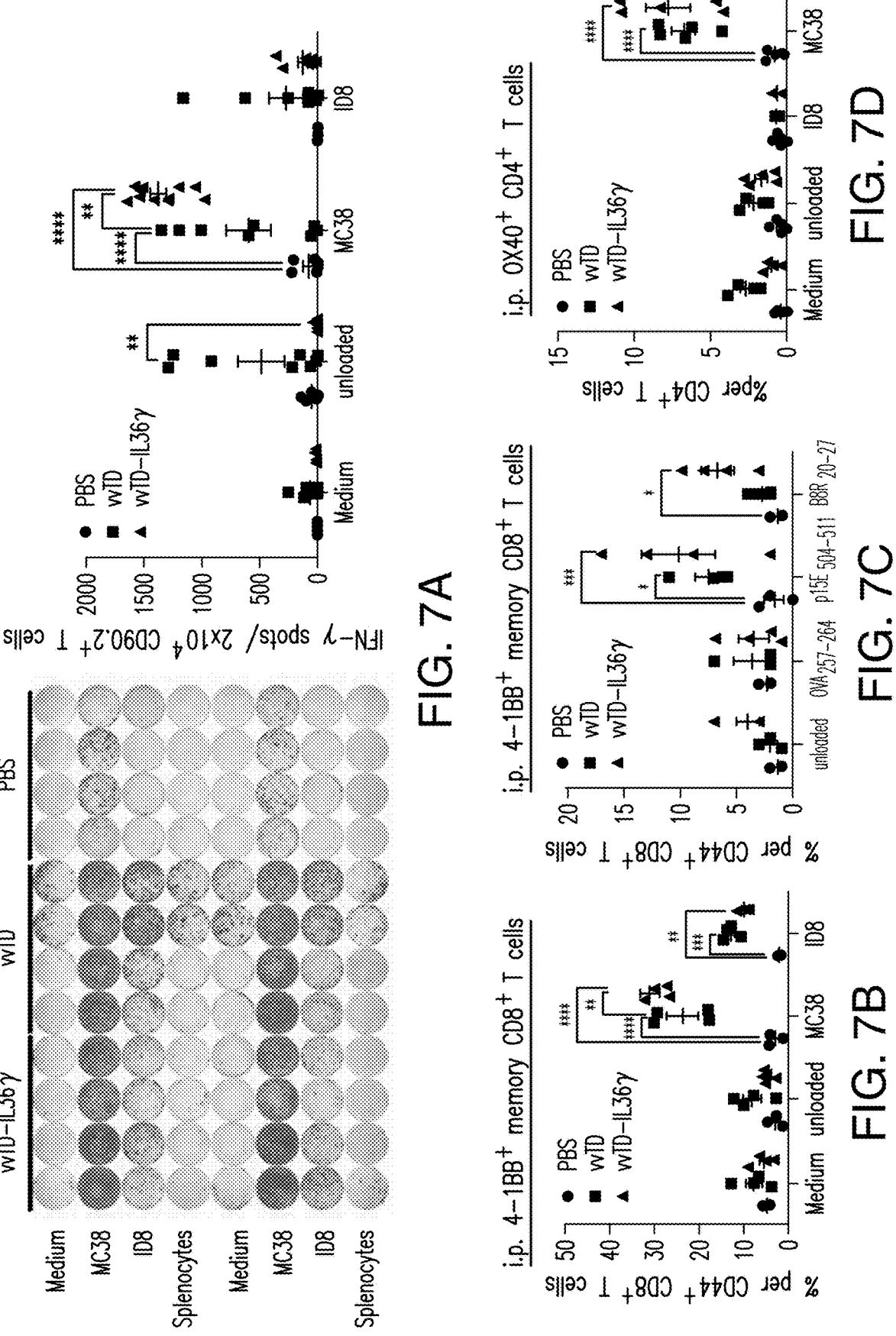
FIGS. 7A-7D provide that vvTD-IL36γ enhanced recognition of murine MC38 colon adenocarcinoma cells by intraperitoneal, memory phenotype $CD8^+$ T cells 11 days after oncolytic virotherapy.

The numbers of tumor antigen-specific T cells were measured in MC38 tumor-bearing mice treated with PBS, vvTD, or vvTD-IL36γ on day 6 post treatment (FIGS. 7A-7D). An IFN-γ ELISPOT assay was performed with T cells co-incubated with radiated tumor cells. Co-incubation with irradiated MC38 cancer cells led to ~520 spots per $2.0 \times 10^4$ T cells for vvTD, and ~1300 spots for vvTD-IL-36γ (p<0.01) (FIG. 7A). When co-incubated with irradiated ID8 ovarian cancer cells (control cells), there were fewer number of spots, suggesting a tumor cell specificity of the T cells. Similar results were obtained using T cells isolated from lavaged specimens or spleens from mice on day 11 after virotherapy (FIGS. 11A-11B).

During anti-tumor and anti-viral adaptive immune response, naive antigen-specific CD8$^+$ T cells undergo a highly orchestrated activation process (Sallusto et al., *Annu Rev Immunol* 22, 745-763 (2004); Farber et al., *Nat Rev Immunol* 14, 24-35 (2014)). It has been shown that activation-induced expression of 4-1BB$^+$ (or CD137$^+$) has accurately identified naturally occurring tumor-reactive T cells in cancer patients (Ye et al., *Clin Cancer Res* 20, 44-55 (2014)), and therefore 4-1BB has been used to identify tumor or viral antigen-specific CD8$^+$ T cells (Wolff et al., *Blood* 110, 201-210 (2007)). The frequency of 4-1BB$^+$CD8$^+$ Tem cells in the tumor microenvironment (FIG. 7B). The present disclosure found that vvTD-IL36γ induced more 4-1BB$^+$ memory CD8$^+$ T cells than vvTD (FIG. 7B) (p<0.01 between vvTD vs vvTD-IL36γ). Next, tumor-antigen- and viral antigen-specific memory CD8$^+$ T cells were examined (FIG. 7C). A tumor-specific self-antigen p15E is selected, which is expressed by endogenous retrovirus in a variety of murine cancer cell lines and defined to function as tumor rejection antigen previously (Huang et al., *Proc Natl Acad Sci USA* 93, 9730-9735 (1996); Kershaw et al., *Cancer Res* 61, 7920-7924 (2001); Shitaoka et al., *Cancer Immunol Res* 6, 378-388 (2018)). The isolated T cells were re-stimulated with a control peptide from OVA (OVA$_{257-264}$), a tumor antigen peptide from P15E (p15E$_{604-611}$), and a viral antigen peptide from B8R (B8R$_{20-27}$). When unloaded or stimulated with OVA, 2-4% of T cells were 4-1BB$^+$CD8$^+$ Tem from mice treated with PBS, vvTD or vvTD-IL-36γ. When re-stimulated with p15E peptide, 4-1BB$^+$CD8$^+$ Tem made up to 2% from mice treated with PBS, ~7.5% with vvTD, and up to 10.5% in vvTD-IL-36γ (FIG. 7C). Similar but somewhat modest increase of viral antigen-specific 4-1BB$^+$ T cells by vvTD-IL-36γ was observed (FIG. 7C). To compare these results with the activation of CD4$^+$ T cells, surface expression of OX40 on CD4$^+$ T cells was examined. Increased percentages of OX40$^+$ CD4$^+$ T cells in the vvTD and vvTD-IL-36γ treatment groups were found after overnight co-culture with MC38 cells as compared to PBS (FIG. 7D). In summary, these results suggested that, compared to the parental OV, IL-36γ-OV increased tumor-antigen-specific T cells, and thereby enhanced antitumor efficacy.

Certain studies have demonstrated that expression of IL-36γ in tumor cells greatly enhanced adaptive antitumor immunity (Wang et al., *Cancer Cell* 28, 296-306 (2015)). Delivery of IL-36γ to the tumor tissue is achieved by the presently disclosed genetically engineered IL-36γ-OV, making IL-36γ therapy more feasible in clinical setting. Insertion of IL-36γ-expressing module has also increased the antitumor efficacy of OVs. The present disclosure provides a combination approach to leverage antitumor activities of both IL-36γ and OVs.

Certain preclinical and clinical studies with OVs indicated that OVs are promising anti-tumor agents, yet improvements in efficacy is needed. One genetically engineered oncolytic VV is vvDD, in which the deletion of two viral genes encoding thymidine kinase and vaccinia growth factors in the viral backbone enhanced its tumor selectivity without diminishing its oncolytic potency (McCart et al., *Cancer Res* 61, 8751-8757 (2001)). However, two phase I clinical trials showed safety but very limited efficacy of vvDD in patients with advanced solid cancer (Zeh et al., *Mol Ther* 23, 202-214 (2015); Down-Canner et a, *Mol Ther* 24: 1492-1501 (2016)). Thus, better VV viral backbones with higher baseline efficacy are needed.

Vaccinia virus has developed a number of immune evasion mechanisms (Guo et al., *J Immunother Cancer* 7, 6 (2019); Smith et al., *J Gen Virol* 94, 2367-2392 (2013); Bidgood et al., *Viruses* 7, 4800-4825 (2015)). Genetic engineering targeting these mechanisms can reduce toxicity, increase tumor specificity, and increase tumor immunogenicity. Therefore, one goal of VV-based immunotherapy is to optimize VV viral vectors to improve immunogenicity. One major immune evasion mechanisms of VV focuses on IL-1 family cytokines (Smith et al., *J Gen Virol* 94, 2367-2392 (2013); Bowie et al., *Proc Natl Acad Sci USA* 97, 10162-10167 (2000) Staib et al., *J Gen Virol* 86, 1997-2006 (2005)). IL-36γ, which is a member of IL-1 gene family and has been shown to induce the expression of IL-1. Addition of IL-36γ improved the OV immunotherapy in several ways. First, compared to control VVs, IL36γ-VVs enhanced tumor site adaptive immune responses by increasing the tumor-infiltration of CD3$^+$ T lymphocytes, including both CD4$^+$ and CD8$^+$ T cells. In addition, IL-36γ promoted qualitative changes such as increases in IFNγ production by CD8$^+$ TIL and DC and decreased M2 TAMs and MDSC. Cell depletion using antibodies against CD4, CD8, and NK1.1 in MC38-tumor model showed that the therapeutic efficacy of this IL-36γ-armed OV depended on both CD4$^+$ and CD8$^+$ T cells, and partially on NK cells too. The present disclosure showed that OV-elicited adaptive antitumor immunity is dependent on CD4$^+$ T cells.

IL-36 not only promoted bulk T cell changes in the tumor microenvironment, but also enhanced antigen specific antitumor immune responses. p15E was used as a representative of tumor antigens for colorectal cancers of mouse and man (Zeh et al., *J Immunol* 162, 989-994 (1999); Foulds et al., *Br J Cancer* 68, 610-616 (1993); Bronte et al., *J Immunol* 171, 6396-6405 (2003); Huang et al., *Proc Natl Acad Sci USA* 93, 9730-9735 (1996); Kershaw et al., *Cancer Res* 61, 7920-7924 (2001); Shitaoka et al., *Cancer Immunol Res* 6, 378-388 (2018)), and B8R was used as a dominant antigen epitope from VV (Moutaftsi et al., *Nat Biotechnol* 24, 817-819 (2006)). When compared to control VV parental virus, IL-36γ-armed VV generated more tumor antigen specific T cells. Interestingly, IL-36γ also increased the number of viral antigen specific T cells. These results indicate that IL-36γ not only improves the adaptive immunity against the tumor cells but also that, against the virus, further ensuring both antitumor efficacy and safety against potential viral infection of the combined therapy. The antiviral immunity can potentiate the immunotherapeutic efficacy against cancer by OVs (Li et al., *Clin Cancer Res* 23, 239-249 (2017); Ricca et al., *Mol Ther* 26, 1008-1019 (2018)).

Material and Methods

Mammalian cell lines. Mammalian cell lines, HEK293, HeLa, HepG2, MDA-MB-468, and CV-1, were originally obtained from ATCC (Manassas, VA). All mammalian cells were grown in Dulbecco's Modified Eagle's Medium (DMEM) supplemented with 100 U/mL penicillin and 100 μg/mL streptomycin, 2 mM L-glutamine, and 10% fetal bovine serum (FBS) (Gemini Bio-Products, West Sacramento, CA) in an incubator at 37° C. with 5% CO2.

Generation of oncolytic VVs expressing recombinant IL-36γ. Plasmid (pcDEF-CD8SP-IL-36γ) contained a hybrid gene encoding the mature peptide (G13-S164) sequence of murine IL-36γ preceded by the human CD8α signal peptide sequence (as BamHI-EcoRI fragment) (Wang et al., *Cancer Cell* 28, 296-306 (2015)). The DNA fragment was PCR amplified from this plasmid and cloned into pCMS1 (Guo et al., *Mol Ther Methods Clin Dev* 7, 112-122 (2017)), which created a new shuttle vector pCMS-IL-36γ. The insert was confirmed by DNA sequencing. In order to create new recombinant VVs in the genetic backbone for deletions of single, double and triple viral genes, CV-1 cells were infected in 6-well plates with wild type (WR strain), vSC20 and vSP viruses at MOI of 0.1 for 2 hours, respectively, and then transfected with the plasmid pCMS-IL-36γ. Two to three days later, the new virus was selected based on the expression of YFP using multiple rounds of flow sorting and plaque purification using CV-1 cells, as described previously (Guo et al., *Mol Ther Methods Clin Dev* 7, 112-122 (2017)). Through these procedures, three novel oncolytic VVs were made with different VV backbones: vvTK-IL-36γ (tk−), vvDD-IL-36γ (tk−/vgf−) and vvTD-IL-36γ (tk−, spi-1- and spi-2-). These three backbone VVs were vvTK- (formerly vJS6), vvDD and vvTD (formerly vSPT) for mutations of viral genes for TK only; both TK and VGF; or triple TK, SPI-1, and SPI-2.

Viral replication in vitro. In vitro viral replication assays comparing IL-36γ-expressing OVs versus the parental ones were performed as described. Briefly, $1.0 \times 10^5$ MC38-luc or other cancer cells/well were plated on 6 well plates and incubated overnight. The cancer cells were then infected with oncolytic VV at MOIs of 0.1 and 1 in 1 mL of 2% FBS-containing DMEM media for 2 hours. The infected cells were harvested after 24, 36, 48, and 72 hours. Following harvest, the cell pellets were homogenized to release intra-cellular virions using Precellys® 24 Tissue Homogenizer (Bertin Instruments, Rockville, MD). The viral load of cell lysates was then determined by viral plaque assay in CV-1 cells.

Oncolysis of cancer cells in vitro. Cancer cells (HepG2, MDA-MB-468 and others) were plated at $1.0 \times 10^4$ cells/well in 96-well plates overnight, and then infected with OV at MOI of 1.0. The number of viable cells were quantified with MTS assays using a kit according to the instruction of the manufacturer (Promega, Madison, WI). As for MC38 colon cancer cells, $2.5 \times 10^5$ cells were plated per well in 6-well plates, and next day infected with OVs at MOI of 0.5. At specified time points (24, 48 and 72-hour), cells in the wells were harvested and viable cells were counted in the presence of trypan blue.

Mice and murine tumor models, and treatments. C57BL/6J mice (B6; $H-2K^b$) of female and 5-6 weeks old, were purchased from the Jackson Laboratory (Bar Harbor, ME). They were housed in the specific pathogen-free conditions at the Animal Facility of the University. For peritoneal carcinomatosis models, B6 mice were injected i. p. with $5.0 \times 10^5$ MC38-luc or $1.0 \times 10^6$ panc02-luc cancer cells, and 5 days later (or as indicated), mice were monitored for tumor growth via in vivo bioluminescence imaging, using Xenogen IVIS Optical In Vivo Imaging System (Caliper Life Sciences, Hopkinton, MA). Then mice were randomly divided into groups for treatments, and injected i.p. with 200 μL PBS, or oncolytic VVs at $1.0 \times 10^8$ pfu/200 μL unless indicated otherwise. Tumor growth was monitored periodically by imaging and health of mice was monitored at least twice a week.

For characterization of infiltrated immune cells, subcutaneous MC38 tumor model was established by injecting $5.0 \times 10^5$ MC38 tumor cells into the right flank of B6 mice. When tumor size reached ~5×5 mm, $1.0 \times 10^8$ pfu of the OV or PBS was injected intra-tumorally. Ten days later, tumor tissues were harvested and processed for immunochemistry for markers of CD3, CD4, CD8 and DAPI staining.

In an additional experiment for depletion of certain types of immune cells, rat-anti-mouse monoclonal antibodies (Ab) were used to selectively deplete certain types of immune cells at indicated time points in the following manner: anti-mouse NK1.1 at 300 μg/injection (clone PK136, BioX-Cell, West Lebanon, NH), anti-mouse CD8 Ab at 250 μg/injection (clone 53-6.7, BioXCell), and anti-mouse CD4 Ab at 150 μg/injection (clone GK1.5, BioXCell) for depletion of NK, $CD8^+$ T cell, and $CD4^+$ T cells, respectively.

Long-term survived mice bearing intra-peritoneal MC38 tumor treated with OVs were used for tumor cell re-challenge (~140 days after initial tumor cell inoculation). In those cured mice and naïve mice (control), $5.0 \times 10^5$ MC38-luc cancer cells were injected subcutaneously onto the right flank, and $5.0 \times 10^5$ Lewis lung cancer cells (LLC) onto the left frank. Tumor appearance was recorded up to day 40 post re-challenge with cancer cells.

Tumor growth was monitored via digital caliper volume measurement and compared to naïve C57BL/6 mice inoculated with MC38-luc tumor implants at the same time. Tumor volume was calculated as: $V_{tumor}$ $(mm^3) = 0.5 (L \times W^2)$.

Flow cytometry and antibodies. BUV395 conjugated anti-mouse CD45 (clone: 30-F11), BUV737 conjugated anti-mouse CD4 (clone: GK1.5), Pacific Blue conjugated anti-mouse CD8α (clone: 53-6.7), PE-CF594 conjugated anti-mouse Foxp3 (MF23), PE conjugated anti-mouse Tim-3 (clone: 5D12), Alexa Fluor 647 conjugated anti-mouse CD206 (clone: MR5D3) were purchased from BD Bioscience. PE-Cy7 conjugated IFN-γ (clone: XMG1.2), FITC conjugated CD11b (M1/70) were purchased from eBioscience. Pacific Blue conjugated anti-mouse MHC II (clone: M5/114.15.2), PE conjugated anti-mouse Gr-1 (clone: RB6-8C5), BV510 conjugated anti-mouse CD24 (clone: M1/69), APC-Cy7 conjugated anti-mouse F4/80 (clone: BM8) were purchased from Biolegend.

At indicated time points, lavaged cells were collected and analyzed by flow cytometry as previously described (Liu et al., *Nat Commun* 8, 14754 (2017)). For IFN-γ staining, cells were stimulated for 4 hours with 50 ng/ml phorbol 12-myristate 13-acetate (PMA, Sigma) and 1 μg/ml ionomycin (Sigma) in the presence of 10 μg/ml Brefeldin A. After stimulation, cells were stained for antibodies against surface markers, followed by fixation permeabilization with Fixiation and Permeabilization buffer (eBioscience, Inc.) according to the manufacturer's instructions. Then cells were stained with antibodies to intracellular markers. All the samples were applied to LSRII or Fortessa FACS (BD Biosciences) and analyzed by using Flowjo software (Tree star).

Live animal imaging. MC38 colon cancer and panc02 pancreatic cancer were previously transduced with a lentivirus expressing firefly luciferase (MC38-luc and panc02-luc) and thus allowed bioluminescence imaging. The growth of transplanted cancers was monitored by in vivo bioluminescent live animal imaging with Xenogen IVIS 200 Optical In Vivo Imaging System (Caliper Life Sciences, Hopkinton, MA). Live animal bioluminescence imaging was performed for two purposes. One was to ensure that tumor implants were present and that groups had comparable tumor burden, and the other was to monitor tumor progression and thus performed periodically after treatments.

Assessment of animal health and survival. Animal health status and survival were monitored closely. Abdominal girth of mice bearing intra-peritoneal tumor implants was monitored with caliper measurement and mice were sacrificed when girth exceeded 1.5× original measurements. Mice either succumbed to their disease or were sacrificed when abdominal girth exceeded allowable measurements as above. Mice with subcutaneous tumors were sacrificed when tumors reached maximum diameter of 2 cm, became ulcerated, and or interfered with murine activity.

Immunofluorescence staining. Resected tumors were fixed for 2 h in 2% paraformaldehyde and incubated in 30% sucrose overnight. Sections were cut (5 μm) and stained with combined primary antibodies CD3 Alexa 488 (100212, Biolegend), CD4 Alexa 594 (100446, Biolegend) and CD8 Alexa 647 (100727, Biolegend) and nuclei were labeled with Hoechst dye (bis benzimide, Sigma B-2283; 1 mg/100 ml in dH20). Images were acquired digitally from 9 fields under each condition. Density of positive cells was evaluated by automated image analysis using Nikon Elements (Nikon Instruments Inc, Melville, NY). Percentage of $CD3^+$ T cells, $CD3^+CD4^+$, $CD3^+CD8^+$ T cells per area has been calculated by number of cells positive for the antibody versus the total number of cells. Student's t-test was used to analyze the statistical significance.

Tumor microenvironment analysis. Once subcutaneous tumors reached 5 mm in diameter, mice were treated intravenously with $1.0 \times 10^8$ pfu of OVs or PBS administered via tail vein injection. Tumor tissues were recovered 2, 4, and 6 days after virus or mock treatment and then homogenized using Precellys® 24 Tissue Homogenizer (Bertin Instruments, Rockville, MD). Single cells were collected for various assays.

RT-qPCR. RNA was isolated from tumor homogenates of subcutaneous MC38-luc tumor implants using RNeasy kit (Qiagen, Germantown, MD). The synthesis of cDNA was then performed using from 2 μg of RNA using gScript™ cDNA SuperMix (Quanta Biosciences, Inc., Gaithersburg, MD) and Dyad® Peltier Thermal Cycler (Bio-Rad, Hercules, CA). Quantitative PCR was then performed using TaqMan analysis with PerfeCTa® qPCR SuperMix (Quanta Biosciences, Inc.) on the StepOnePlus System (Life Technologies, Grand Island, NY). All PCR primers were purchased from Thermo Fisher Scientific (Waltham, MA).

Relative gene expression was compared to a housekeeping gene, either hypoxanthine-guanine phosphoribosyltransferase (HPRT1) or glyceraldehyde 3-phosphate dehydrogenase (GAPDH), and was expressed as fold increase ($2^{-\Delta CT}$), where $\Delta CT = CT_{(Target\ gene)} - CT_{(HPRT1\ or\ GAPDH)}$.

IFN-γ ELISPOT assays. Briefly, at day 7 or indicated time after inoculation of 0.5e 6 of MC38-luc colon tumor cells intraperitoneally, tumor-bearing mice were treated i.p. with 1.0e8 pfu of oncolytic OVs, or PBS. On the specific time as indicated, intra-peritoneal lavage was performed during which 5 mL of 2% FBS-containing PBS was injected into the peritoneal cavity using an 18-gauge needle, and then the cavity was gently agitated before the volume was aspirated and repeated up to 2 times. Lavage fluid was collected and strained over 100 μM cell strainer, and red blood cells were lysed using ACK Lysing Buffer and then straining over 40 μM cell strainer. The $CD8^+$ T cell population from $2.0 \times 10^7$ cells in the lavage was then isolated using α-mouse CD8 microbeads isolation protocol (Millenl Biotec, San Diego, CA). Once isolated, $2.0 \times 10^4$ $CD8^+$ T cells were stimulated with 4,000-rad-irradiated MC38 cells or control cancer cells (at $2.0 \times 10^4$) in RPMI 1640 media supplemented with 10% FBS at 37° C., 5% $CO_2$ for 24 h. Following incubation, the plates were appropriately washed, and then incubated with biotinylated α-mouse IFN-γ antibody (mAb R4-GA2-Biotin, Mabtech, Inc., Cincinnati, OH). The plates were developed using Vectastain Elite ABC and AEC Peroxidase substrate (SK-4200) kits according to vendor protocols (Vector Laboratories, Inc. Burlingame, CA). Finally, the plates were read and analyzed using an ImmunoSpot™ analyzer and software (Cellular Technology, Ltd., Shaker Heights, OH).

Statistical analyses. GraphPad Prism version 7 (GraphPad Software, Inc., San Diego, CA) was used to analyze the experimental data. Analysis was performed using non-parametric Student's t test. Survival of animals was assessed using Kaplan-Meier survival curves and was analyzed using log rank (Mantel-Cox) test. A p value of <0.05 was considered statistically significant. The standardized symbols were used in the figures, as follows: *$p<0.05$; $p<0.01$; *$p<0.001$; ****$p<0.0001$; and NS: not significant.

Although the presently disclosed subject matter and certain of its advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, and composition of matter, and methods described in the specification. As one of ordinary skill in the art will readily appreciate from the disclosure of the presently disclosed subject matter, processes, machines, manufacture, compositions of matter, or methods, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, or methods.

Various patents, patent applications, publications, product descriptions, protocols, and sequence accession numbers are cited throughout this application, the disclosure of which are incorporated herein by reference in their entireties for all purposes.

What is claimed is:

1. An oncolytic vaccinia virus comprising a recombinant nucleic acid molecule encoding interleukin-36γ (IL-36γ), wherein the oncolytic vaccinia virus lacks the expression of a functional thymidine kinase (TK), wherein the recombinant nucleic acid molecule is operably linked to a promoter.

2. The oncolytic virus of claim 1, wherein the recombinant nucleic acid molecule is integrated into the genome of the oncolytic virus.

3. The oncolytic virus of claim 1, wherein the oncolytic vaccinia virus:
   a) comprises a mutation of a J2R gene;
   b) lacks the expression of a functional vaccinia growth factor (VGF);
   c) comprises a mutation of a C11R gene;
   d) lacks the expression of a functional serine proteinase inhibitor 1 (SPI-1);
   e) comprises a mutation of a B22R gene;
   f) comprises a mutation of a B13R gene; and/or
   g) lacks the expression of a functional serine proteinase inhibitor 2 (SPI-2).

4. The oncolytic virus of claim 3, wherein the recombinant nucleic acid molecule is integrated into the locus of the J2R gene.

5. The oncolytic virus of claim 3, wherein the oncolytic vaccinia virus lacks the expression of the functional TK and the expression of the functional VGF.

6. The oncolytic virus of claim 3, wherein the oncolytic vaccinia virus comprises the mutation of the J2R gene and the mutation of the C11R gene.

7. The oncolytic virus of claim 3, wherein the oncolytic vaccinia virus lacks the expression of the functional TK, of the functional SPI-2, and of the functional SPI-1.

8. The oncolytic virus of claim 3, wherein the oncolytic vaccinia virus comprises the mutation of the J2R gene, the mutation of the B22R gene, and the mutation of the B13R gene.

9. The oncolytic virus of claim 1, wherein the oncolytic vaccinia virus is a Western Reserve strain.

10. A pharmaceutical composition comprising the oncolytic virus of claim 1.

11. The pharmaceutical composition of claim 10, further comprising an immunomodulatory agent.

* * * * *